(12) United States Patent
Groger et al.

(10) Patent No.: US 6,300,638 B1
(45) Date of Patent: Oct. 9, 2001

(54) MODULAR PROBE FOR TOTAL INTERNAL REFLECTION FLUORESCENCE SPECTROSCOPY

(75) Inventors: Howard P. Groger, Gainesville, FL (US); John Raymonda, Las Cruces, NM (US); K. Peter Lo, Blacksburg, VA (US); Roger L. Reynolds, Blasdell; William F. Sullivan, Cheektowaga, both of NY (US); Myron T. Coolbaugh, Christiansburg, VA (US)

(73) Assignees: Calspan SRL Corporation, Buffalo, NY (US); American Research Corporation of Virginia, Radford, VA (US)

( * ) Notice: Subject to any disclaimer, the term of this patent is extended or adjusted under 35 U.S.C. 154(b) by 0 days.

(21) Appl. No.: 09/189,841

(22) Filed: Nov. 12, 1998

(51) Int. Cl.⁷ .................................................. G01N 21/64

(52) U.S. Cl. .............................................. 250/458.1

(58) Field of Search ......................................... 250/458.1

(56) References Cited

U.S. PATENT DOCUMENTS

| Re. 31,879 | 5/1985 | Lubbers et al. | 436/133 |
|---|---|---|---|
| 4,035,082 | 7/1977 | Kirschen | 356/114 |
| 4,050,895 | 9/1977 | Hardy et al. | 23/230 R |
| 4,548,907 | 10/1985 | Seitz et al. | 436/163 |
| 4,549,807 | 10/1985 | Hoffmaster | 356/318 |
| 4,582,809 | 4/1986 | Block et al. | 436/527 |
| 4,594,511 | 6/1986 | Cooper et al. | 250/339 |

(List continued on next page.)

FOREIGN PATENT DOCUMENTS

| 300481 A7 | 6/1992 | (DE) . |
|---|---|---|
| 60-125544 A | 7/1985 | (JP) . |

OTHER PUBLICATIONS

Weiss et al., "Thin Film Monitoring Using Surface Plasmon Resonance Waveguide Sensors," pp. 1–20, Photonics Research Laboratory, University of Florida, Gainesville, Fl.

Kelsch, James A., "Computer Block Diagram", Computer BMP, Arcova, Gainesville, FL No date.

Haruvy et al., "Sol–Gel Preparation of Optically Clear Supported Thin–Film Glasses Embodying Laser Dyes", 1992, Chapter 28, pp. 405–424, Supramolecular Architecture, USA.

Levy, David, "Sol–gel glasses for optics and electro–optics", Journal of Non–Crystalline Solids, Section 10, 147–148 (1992) pp. 508–517, North Holland.

Reisfeld et al., "Optical Properties of Colorouts or Luminescent Species in Sol–Gel Glasses", Structure and Bonding 77, Springer–Verlag, 1992, pp. 239–247, Berlin, Heidelberg.

Zusman et al, "Doped Sol–Gel Glasses as Chemical Sensors", Journal of Non–Crystalline Solids, vol. 122, 1990, pp. 107–109, North Holland.

Tanguay, Armand R., Jr., "Integrated Optical Information Processing", Final Research Report 1988, USC Optical Materials and Devices Laboratory, pp. 62–71, Los Angeles, CA.

(List continued on next page.)

Primary Examiner—Constantine Hannaher
(74) Attorney, Agent, or Firm—Steptoe & Johnson LLP

(57) ABSTRACT

An instrument for total internal reflection fluorescence spectroscopy having modular probe that inexpensively monitors vapors and liquid-phase analytes under field conditions is described. The system is particularly helpful in evaluating multiple analytes using the fluorescence of a material immobilized in a thin sorbent polymer coating. At the same time, the system is capable of monitoring trace quantities of analyte using a fluorescence-read immunological reaction. The device includes a diode laser source, a shaped optical element (which may be as simple as a microscope slide), and one or more amplified photodiode detectors. The shaped optical element propagates light from the diode laser in a series of internally reflective bounces.

119 Claims, 16 Drawing Sheets

U.S. PATENT DOCUMENTS

| | | |
|---|---|---|
| 4,651,010 | 3/1987 | Javan . |
| 4,654,532 | 3/1987 | Hirschfeld ........................ 250/458.1 |
| 4,716,121 | 12/1987 | Block et al. .......................... 436/514 |
| 4,737,464 | 4/1988 | McConnell et al. .................. 436/43 |
| 4,752,115 | 6/1988 | Murray, Jr. et al. .............. 350/96.29 |
| 4,775,214 | 10/1988 | Johnson ............................ 350/96.29 |
| 4,793,977 | 12/1988 | Morris . |
| 4,803,049 | 2/1989 | Hirschfeld et al. ..................... 422/58 |
| 4,815,843 | 3/1989 | Tiefenthaler et al. ............... 356/128 |
| 4,818,710 | 4/1989 | Sutherland et al. ................. 436/527 |
| 4,844,613 | 7/1989 | Batchelder et al. ................. 356/318 |
| 4,852,967 | 8/1989 | Cook et al. ........................ 350/96.29 |
| 4,877,747 | 10/1989 | Stewart ................................ 436/525 |
| 4,880,752 | 11/1989 | Keck et al. ............................... 435/7 |
| 4,889,690 | 12/1989 | Optiz et al. ............................ 422/73 |
| 4,925,268 | 5/1990 | Iyer et al. . |
| 4,929,561 | 5/1990 | Hirschfeld ........................... 436/116 |
| 4,980,278 | 12/1990 | Yamada et al. ........................... 435/7 |
| 4,997,278 | 3/1991 | Finlan et al. ......................... 356/128 |
| 5,004,913 | 4/1991 | Kleinerman .......................... 250/227 |
| 5,019,350 | 5/1991 | Rhum et al. ....................... 422/82.07 |
| 5,019,518 | 5/1991 | Diehl et al. . |
| 5,021,661 | 6/1991 | Masutani .............................. 250/339 |
| 5,023,053 | 6/1991 | Finlan ................................ 422/82.05 |
| 5,030,832 | 7/1991 | Williams et al. .................. 250/458.1 |
| 5,032,380 | 7/1991 | Novak et al. . |
| 5,035,863 | 7/1991 | Finlan et al. ....................... 422/82.05 |
| 5,039,492 | 8/1991 | Saaski et al. ....................... 422/82.09 |
| 5,043,585 | 8/1991 | Fehrenbach et al. ............. 250/458.1 |
| 5,045,282 | 9/1991 | Kritzman et al. ....................... 422/56 |
| 5,055,265 | 10/1991 | Finlan ................................ 422/82.05 |
| 5,061,857 | 10/1991 | Thompson et al. ............... 250/458.1 |
| 5,063,297 | 11/1991 | Hardenbrook et al. ........... 250/458.1 |
| 5,067,788 | 11/1991 | Jannson et al. ........................... 385/2 |
| 5,071,248 | 12/1991 | Tiefenthaler et al. ............... 356/128 |
| 5,093,266 | 3/1992 | Leader et al. ........................... 436/68 |
| 5,094,517 | 3/1992 | Franke .................................. 385/12 |
| 5,094,959 | 3/1992 | Allen et al. .......................... 436/172 |
| 5,095,514 | 3/1992 | Curtis .................................... 385/12 |
| 5,096,671 | 3/1992 | Kane et al. ......................... 422/82.07 |
| 5,114,676 | 5/1992 | Leiner et al. ....................... 422/82.06 |
| 5,120,131 | 6/1992 | Lukosz .................................. 356/136 |
| 5,127,405 | 7/1992 | Alcala et al. ......................... 128/633 |
| 5,154,890 | 10/1992 | Mauze et al. ...................... 422/82.07 |
| 5,156,972 | 10/1992 | Issachar ................................ 435/288 |
| 5,156,976 | 10/1992 | Slovacek et al. ..................... 436/164 |
| 5,166,515 | 11/1992 | Attridge .......................... 250/227.25 |
| 5,170,448 | 12/1992 | Ackley et al. .......................... 385/31 |
| 5,195,162 | 3/1993 | Sultan et al. .......................... 385/130 |
| 5,196,709 | 3/1993 | Berndt et al. ...................... 250/458.1 |
| 5,206,175 | 4/1993 | Rossmann et al. . |
| 5,212,386 | 5/1993 | Gratton et al. .................... 250/458.1 |
| 5,227,134 | 7/1993 | Janata ................................ 422/82.08 |
| 5,237,631 | 8/1993 | Gavish et al. .......................... 385/12 |
| 5,245,411 | 9/1993 | Yuste et al. ........................... 356/445 |
| 5,270,548 | 12/1993 | Steinkamp ........................ 250/461.2 |
| 5,302,349 | 4/1994 | Dandliker et al. ................ 422/82.08 |
| 5,307,146 | 4/1994 | Porter et al. .......................... 356/320 |
| 5,307,148 | 4/1994 | Kambara et al. ..................... 356/344 |
| 5,308,581 | 5/1994 | Lippitsch et al. ................. 422/82.08 |
| 5,313,264 | 5/1994 | Ivarsson et al. ....................... 356/73 |
| 5,315,122 | 5/1994 | Pinsky et al. ...................... 250/461.2 |
| 5,315,672 | 5/1994 | Padovani ............................... 385/12 |
| 5,317,162 | 5/1994 | Pinsky et al. ...................... 250/461.2 |
| 5,322,798 | 6/1994 | Sadowski .............................. 436/113 |
| 5,323,010 | 6/1994 | Gratton et al. .................... 250/458.1 |
| 5,324,635 | 6/1994 | Kawase et al. ....................... 435/7.94 |
| 5,327,225 | 7/1994 | Bender et al. ........................ 356/445 |
| 5,340,715 | 8/1994 | Slovacek et al. ........................ 435/6 |
| 5,344,784 | 9/1994 | Attridge ............................... 436/518 |
| 5,359,681 | 10/1994 | Jorgenson et al. ..................... 385/12 |
| 5,376,554 | 12/1994 | Vo-Dinh . |
| 5,424,841 | 6/1995 | Van Gelder et al. ................ 356/417 |
| 5,447,845 | 9/1995 | Chu et al. ................................. 435/6 |
| 5,489,988 | 2/1996 | Ackley et al. ........................ 356/436 |
| 5,532,493 * | 7/1996 | Hale et al. ......................... 250/458.1 |
| 5,548,124 | 8/1996 | Takeshima et al. .............. 250/458.1 |
| 5,577,137 | 11/1996 | Groger et al. .......................... 385/12 |
| 5,606,170 * | 2/1997 | Saaski et al. ...................... 250/458.1 |
| 5,606,633 | 2/1997 | Groger et al. .......................... 385/12 |
| 5,640,470 | 6/1997 | Iyer et al. . |
| 5,745,231 | 4/1998 | Groger et al. ........................ 356/432 |
| 5,757,013 | 5/1998 | Groger et al. ..................... 250/458.1 |

OTHER PUBLICATIONS

Haruvy et al., "Supported sol–gel thin–film glasses embodying laser dyes II: Three–layered waveguide assemblies", SPIE, vol. 1590, Submolecular Glass Chemistry and Physics, 1991, pp. 59–70.

Groger et al., "Polymeric Sensor Materials for GB and DMMP Detection", ERDEC Scientific Chemical Conference on Biological Defense Research, 1996, pp. 37–43.

Otsuki et al., "Characterization of Nafion Solution and Films and Observation of the Casting Process Using Basic Dyes as Optical Probes," *Journal of Applied Polymer Science*, 1995, pp. 697–705, vol. 56, John Wiley & Sons, Inc., USA.

Nestmann et al., "Mutogenicity in Salmonella of Dyes Used by Defence Personnel for the Detection of Liquid Chemical Warfare Agents," *Carcinogenesis*, 1981, pp. 879–883, vol. 2, No. 9, IRL Press Limited, London, UK.

Shea et al., "Fluorescence Probes for Evaluating Chain Solvation in Network Polymers. An Analysis of the Solvatochromic Shift and the Dansyl Probe in Macroporous Styrene–Divinylbenzene and Styrene–Diisopropenylbenzene Copolymers," *Macromolecules*, 1989, pp. 1722–1730, vol. 22, American Chemical Society, USA.

McGill et al., "Solvatochroism. A New Method for Polymer Solubility and Sorption Characterisation," *Polymer Preprints*, 1990, pp. 578–579, vol. 31, No. 2, American Chemical Society Division of Polymer Chemistry, USA.

Paley et al., "Solvatochroism. A New Method for Polymer Characterization," *Macromolecules*, 1990, pp. 4557–4564, vol. 23, AMerican Chemical Society, USA.

Dong et al., "A Rapid and Sensitive Fluorescence Method for Detection and Analysis of Soman," *Junshi Yixue Kexueyuan Yuankan*, 1993, pp. 301–303, vol. 17.

Czarnaski et al., "Solid State Fluorometer: Prototype Development," Report 1994, SAIC–01–0262–01–1222, AL/OE–TR–1993–0162, US Department of Commerce.

Grate et al., "The Predominant Role of Swelling–Induced Modulus Changes of the Sorbent Phase in Determining the Responses of Polymer–Coated Surface Acoustic Wave Vapor Sensors," *Analytical Chemistry*, 1992, pp. 610–624, vol. 64, American Chemical Society, USA.

McGill et al., "Solvatochromic Characterization of Polymers, Effects of Relative Humidity," *Macromolecules*, 1992, pp. 3015–3019, vol. 25, American Chemical Society, USA.

Chang et al., "Fluorescence Lifetime–based Sensing of Methanol," *Analyst*, 1997, pp. 173–177, vol. 122.

Mangino et al., "Experimental Examination of the Relationship Between Exposure and Desorption of VX from Material Surfaces", Abstract No. 54902e, *Chemical Abstracts*, Jul. 28, 1997, p. 1076, vol. 127 No. 4, American Chemical Society, USA.

Groger et al., "Thin Film Sensors to Evaluate Chemical and Biological Threats to Army Structures", Feb. 1992, pp. 1–41, American Research Corporation of Virginia, Radford, VA.

Churchill et al., "Self-assembled Thin Film Sensors for Aquaculture Process Control", SBIR Phase I Final Report, Dec. 30, 1992, pp. 1–55, American Research Corporation of Virginia, Radford, VA.

Jahns et al., "Integrated planar optical imaging system with high interconnection density", Optical Letters, vol. 18, No. 19, Oct. 1, 1993, pp. 1594–1596.

Feddersen et al., "Digital parallel acquisition in frequency domain fluorimetry", Rev. Sci. Instrucm., vol. 60, No. 9, Sep. 1989, pp. 2929–2936.

Chen et al., "1–to–12 surface normal three–dimensional optical interconnects", Applied Physics Letters, vol. 63, No. 14, Oct. 1993, pp. 17–19.

* cited by examiner

MODULAR PROBE FOR TOTAL INTERNAL REFLECTION FLUORESCENCE SPECTROSCOPY

BACKGROUND OF THE INVENTION

The present invention is a chemical and biological sensor based on optical methods of detection.

Needs exist for rapid, sensitive methods of detection and monitoring of chemical and biological warfare materials. Candidate chemical warfare sensors and biological warfare detection instruments should be small, have few or no moving parts, and should be amenable to use in joint chemical and biological detection.

Optical chemical and biological sensors are used in a network of point detectors for a range of applications including monitoring decontamination of Army field structures, detection of chemical and biological agents in chemical treaty verification (see Table I), reconnaissance of battlefield and depot perimeters, demilitarization procedures and monitoring breakthrough times associated with polymeric or other complex structural materials. Selected tasks associated with each application and sensitivities required are presented in Table II.

At present, sensors are available that are capable of meeting the requirements of several applications but no sensor has provided the combined sensitivity and speed of response necessary for each application. Needs exist for field-usable chemical and biological sensors for the detection of vapor and liquid dispersed chemical warfare agents, toxins of biological origin and aerosol-dispersed pathogenic micro-organisms. Existing instrumentation used in identifying chemical warfare agents rely upon ion mobility spectroscopy (IMS) or gas chromatography for detection. The advanced chemical agent detection/alarm system (ACADA) uses ion-mobility spectroscopy to achieve sensitivities to GB/GD on the order of 1.0 mg/m$^3$ (170 ppb) in 10 seconds and 0.1 mg/m$^3$ (17 ppb) in 30 seconds. The size and weight characteristics of the ACADA system 0.028 cubic meter (1 cubic foot) in volume and 11.34 kilograms (25 pounds) in weight reduce the applicability of this instrument for distributed sensing or remote sensing applications. Sensors such as the miniCAMS system provide unparalleled sensitivity but require preconcentration times on the order of minutes which are unsuitable for rapid detection of conditions that are immediately dangerous to life and health (IDLH). Other methods under consideration use acoustic or optical/electrochemical methods of detection such as surface acoustic wave (SAW)-based instruments and light addressable potentiometric sensor (LAPS) (Hafeman et aL, 1988). The SAW instrument has demonstrated sensitivities to GB/GD at 0.01 mg/m$^3$ (1.7 ppb) but requires preconcentration times of from 2 minutes to 14 minutes. Both SAW and LAPS systems have been used in conjunction with immunoassay procedures to detect organophosphorus chemical agents (Rogers et al., 1991; Mulchandani and Bassi, 1995).

Optical methods of detecting organophosphorus-based nerve agent materials have been reviewed by Crompton (1987). One of the best calorimetric methods for detection of organophosphorus halides involves the use of diisonitrosoacetone reagent or the monosodium salt of this material which upon exposure to GA Tabun or GB Sarin at concentrations of micrograms per milliliter produces a magenta color with maximum response within seven minutes. Chemical analysis using 3-aminophthalkydrazide (luminol) with sodium perborate has been shown to be effective in detecting as little as 0.5 microgram of GB Sarin or GA Tabun. The use of polymer-coated optical waveguides in the detection of nerve agents or simulated nerve agents such as dimethyl methylphosphonate (DMMP) has been reported by Giuliani et al. (1986), who identified polymeric materials with an affinity for the nerve agent exhibiting a change in refractive index upon absorption of the nerve agent. Several materials have been found to exhibit an affinity for DMMP. Fluoropolyol, described by Grate and Abraham (1991), was found to have a partition coefficient for vapor phase DMMP between one million and ten million indicating that the concentration of DMMP in the fluoropolyol was up to ten million times that in the vapor phase. Fluoropolyol is strongly acidic, a factor that improves sensitivity to strongly basic vapors such as the organophosphorus compounds.

Fluorescence methods of chemical characterization rely for their operation on the use of light energy of intensity, $I_{ex}$, to excite a fluorescent molecule from a ground state $E_0$ to an excited state $E^*$. Molecules of the fluorophore decay from the excited state either through nonradiative energy transfer, emission of heat or radiative emission of a photon at a wavelength, $\lambda_{em}$, longer than that of the excitation source $\lambda_{ex}$. At low concentrations of the fluorophore, the intensity of the fluorescence emission, $I_{em}$, is directly proportional to the incident light intensity through $$I_{em} = Q\, I_{ex}\, (1 - \exp(-\epsilon bc)) \tag{1}$$

where Q is the quantum yield of the fluorophore, $\epsilon$ is the molar absorptivity, b is the path length and c is the concentration of the fluorophore. The sensitivity of optical sensors to chemical and biological agents can be increased by restricting the excitation energy to a limited volume or area, by increasing the collection efficiency or by increasing the intensity of the excitation source. For this reason, several total internal reflection techniques have been developed to improve solid surface chemical assays (Kronick and Little, 1975; Andrade et al., 1985). Total internal reflection is the phenomenon occurring when light originating in an optically dense region with a refractive index, $n_i$, impinges upon a boundary separating the dense medium from a less-dense medium with refractive index, $n_r$. For a small angle between the incident light and the normal to the interface, a certain amount of light is transmitted and the remainder is reflected. As the incidence angle, $\theta$, exceeds a critical value, $\theta_C$, given by Snell's law, $$\theta_C = \sin^{-1} \frac{n_t}{n_i} \tag{2}$$

the magnitude of the transmitted beam decreases to zero, and all of the light is internally reflected. For silicon nitride on silica on silicon waveguides, the refractive index of the waveguiding layer of silicon nitride is approximately 1.99 and the refractive index of the silica is 1.46. The critical angle is 47.2°. For ion-exchanged soda lime glass, the refractive index of the base material is 1.512 and the refractive index of the silver ion-exchanged glass is 1.605. If a step-index waveguide is produced, the critical angle is 70.4°. The critical angle is decreased by increasing the refractive index difference between the base material and waveguide. In total internal reflection, the excitation intensity, I, of the evanescent wave varies with distance from the interface in the less-dense medium as the inverse exponential of the distance, x, over a characteristic depth, d, as follows $$I(x)\, I_0 e^{-x/d} \tag{3}$$

where $I_0$ is the light intensity at the surface. The penetration depth, d, of the evanescent field is controlled by the excitation wavelength, $\lambda_0$, the refractive indices of the media and the angle of incidence, $\theta$, according to the equation, $$d = \frac{\lambda_0}{2\pi}[n_i^2\sin^2\theta - n_t^2]^{-1/2} \quad (4)$$

An optical sensor is used to detect chemical warfare agents through detection of changes in fluorescence upon exposure to the agent of a fluorophore immobilized in a solid matrix. The use, as chemical sensors, of fluorophores immobilized in polymeric matrices has been reviewed by Wolfbeis (1985) and Taib and Narayanaswamy (1995), among others.

An array of sensitive non-selective sensors, each having a differential response to the analyte of interest, is used to identify selectively that analyte and provide a quantitative measure of the concentration of the analyte. That principle has been demonstrated by Grate et al. (1993) and Rose-Pehrsson et al. (1988) in the use of an array of surface acoustic wave sensors to detect organophosphorus and organosulfur analytes at low concentrations. Similarly, work has been performed by Freund and Lewis (1995) to characterize odorant materials using the change in the electrical characteristics of an array of poly(pyrrole) conducting polymer-based capacitive probes. Arrays of resistors based on carbon black incorporated in a range of polymeric materials have been shown to be sensitive to parts-per-thousand levels of various solvent vapors. Data reported by researchers at Tufts University (Dickinson et al., 1996; White et al., 1996) demonstrated that an array of cross-reactive fluorescence-based sensors could be used to measure selectively the concentration of organic vapors in an air stream.

Vapor solubility parameters are matched with polymer solvent phase solubility parameters to provide probe materials with large partition coefficients for the vapors of interest. The approach to selecting polymer materials for use in chemical sensors is provided by McGill et al. (1994), and is based on prediction of partition coefficient using the linear salvation energy relationship (LSER). The relationship between the log of the gas-polymer partition coefficient, $K_p$, and a number of solvation parameters is given by $$\text{Log}K_p=C+rR_2+s\pi H_2+a\alpha H_2+b\beta H_2+l\text{Log}L^{16} \quad (5)$$

where $R_2$ is the excess molar refraction, a term which models polarizability contributions from n and n electrons, $\pi H_2$ is the dipolarity, $\alpha H_2$ is the hydrogen bond acidity, $\beta H_2$ is the hydrogen bond basicity, $L^{16}$ is the gas-liquid partition coefficient of hexadecane and a, b, l, r and s are coefficients relating the solvation properties of the polymer to those of the vapor. The regression constant, c, is used to allow empirical fitting of the data. Coefficients for many polymeric materials have been determined using partition coefficients calculated from gas-liquid chromatographic retention data at high temperatures in inert atmospheres (Patrash and Zellers, 1993). It has been determined by McGill et al. (1994) that selectivity of polymeric sorbent layers can be optimized by evaluating ratios of LSER coefficients. Table III contains laser regression coefficients for fourteen polymers at 25° C. For example, although each of the partition coefficients of fluoropolyol, 1-(4-hydroxy, 4-trifluoromethyl,5,5,5,-trifluoropentene and poly(4-vinylhexafluorocumyl alcohol) for dimethyl methylphosphonate a simulant for alkylphosphonate nerve agents, is relatively high, the relative magnitudes of the partition coefficients are arranged in the order of the ratio of acidity to basicity.

Needs exist generally for identifying industrial or polluting chemicals in liquid, gas or vapor forms. Needs also exist for detectors for chemical and biological warfare agents meeting a wide range of advanced specifications. Those specifications include reduction in size and weight of chemical agent detection instrumentation, development of chemical agent monitors that can be used with water supplies, integration of chemical and biological warfare detection instrumentation, development of miniature instrumentation with few or no moving parts and reduction in detector cost to provide distributed wide area networks for advanced warning capability. The defense against chemical and biological warfare agents involves detection of potential threats, development and utilization of protective equipment, development of vaccination and post-exposure prophylaxis measures and fabrication of structures with barriers to the toxic agents which are suitable for decontamination procedures. Threat identification is necessary prior to engagement, during battle and after battle during decontamination procedures. Additional uses of sensors for chemical warfare materials may be found in treaty verification, demilitarization, environmental monitoring and characterization of materials acting as barriers to agent diffusion.

Several methods are currently available for long-range threat identification using laser-based techniques such as light detection and ranging (LIDAR) and for laboratory analysis of chemical warfare agents using gas chromatography (miniCAMS), surface acoustic wave (SAW) technology or ion mobility sensor (IMS) technology, or for biological agent monitoring using light addressable potentiometric sensor (LAPS) or chemiluminescence approaches. There remains a need for lightweight, high-sensitivity sensors with rapid response times for use in threat identification, area monitoring, special forces operations, decontamination, demilitarization, treaty verification requirements and antiterrorism.

SUMMARY OF THE INVENTION

An instrument for total internal reflection spectroscopy having a modular probe provides inexpensive and reliable monitoring of gases, vapors and liquid-phase analytes under field conditions. The system is particularly helpful in the evaluation of multiple analytes using the fluorescence of probe material immobilized in a thin sorbent polymer coating. The system is capable of monitoring trace quantities of analyte using fluorescence-read immunological reaction. The device includes a diode laser source, an optional variable transmission neutral density filter, an optional focusing element, a shaped optical element (which may be as simple as a microscope slide with a beveled edge), one or more amplified photodiode detectors, one or more wavelength selective optical filters, and one or more lock-in amplifiers. The shaped optical element propagates light from the diode laser in a series of internally reflective bounces. The probe is optimized when the angle between the normal to the bevel and incidence of the laser beam is 15 to 20°.

The system is used to detect changes in fluorescence resulting from interaction with gas phase, liquid phase or vapor phase analytes. When looking for volatile compounds in water, the following procedure is used. The sample is filtered and is input to a vaporization chamber. The chamber contains a thin-film heater and two valves. One valve restricts fluid from exiting along the sample train. The other valve restricts fluid from entering the detection chamber. With sample in the vaporization chamber, the thin-film heater is turned on with the two valves closed. Because the chamber is less than 500 µm across, 500 µm deep and less than 10 mm long, the material is rapidly vaporized, providing a short pulse of sample available to the detector. The short pulse can be used in monitoring the detector response.

The sorbent polymer coating is deposited on the shaped optical element such that the immobilized fluorophore is excited through the evanescent field of the laser beam. When the shaped optical element is fabricated from soda-lime glass, the surface is prepared using a solvent cleaning or acid cleaning method.

The modular probe contains a flow cell used for vapor samples or modified for liquid samples. Fluorophore-polymer volumes drop cast on the surface of the shaped optical element provide unusually high sensitivities when monitored using the lock-in amplifier apparatus. The instrument uses either a beam splitter or line generator after the diode laser to spread the laser beam to allow multiple channels of detection. For a 2.54 cm by 7.62 cm shaped optical element, parallel beams would enter at the bevel and travel along the element. As an example, along the 2.54 cm length of the bevel plate, as many as 8 stripes are formed. These stripes are formed from a range of polymer and fluorophore materials sensitive to each of the analytes of interest. Multiple photodiodes detect the fluorescence from each stripe. Each photodiode is monitored using a digital signal processing apparatus. A digital-signal processing technique is used for low-intensity fluorescence detection. The diode laser is modulated at a frequency from 500 Hz to 5000 Hz. The fluorescence and residue excitation signals are separated and detected as different channels. The signal for each channel is fed into a 4-pole Butterworth active band-pass filter to reject interference noise signals from ambient light, and the analog signal is converted to a digital signal by the DSP onboard 12-bit analog-to-digital conversion interface circuit. A 256 point complex FFT is used to convert the time-domain data to frequency domain data using a DSP chip. The frequency window is selected, and the remainder of the frequency data is set to zero. The resultant frequency spectrum is inverse fast Fourier transformed back to the time domain.

The ratio of the fluorescence and excitation channels are read out by utilizing the logarithmic outputs of the DSP chips. Channels A and B denote the logarithm of the outputs from the fluorescence signal and the excitation signal, respectively. The difference of the two channels Channel A−Channel B=Log(Fluorescence)−Log(Excitation)=Log-(Fluorescence/Excitation)

thus, represents the logarithm of the ratio of fluorescence to the excitation signal. The difference of the two analog signals is implemented electronically using a unity gain difference amplifier circuit.

A variation on the total internal reflection fluorescence (TIRF) Instrument involves monitoring of the autocorrelation function of the fluorescence and scattering signals received from the TIRF using a fluorescence fluctuation technique.

In a preferred fluorescence instrument, a semiconductor diode laser is used to illuminate a shaped optical element. The fluorescence is generated from a fluorophore deposited within the evanescent field of the shaped optical element. The fluorescence go is excited using light in the wavelength range 635 nm to 1060 nm. The fluorescence is detected using an amplified photodiode. Preferably, there is a focusing lens between the laser and the shaped optical element. The shaped optical element may be a microscope slide. The shaped optical element may be a polymer formed by injection molding. The molded plastic has a scratch/dig of 60/40 or less. In a preferred form, the shaped optical element is polystyrene with a refractive index of 1.59. Preferably, the shaped optical element has beveled edges. The angle of the bevel is such that the normal to the bevel surface is 10 to 20 degrees from the angle of incidence of the diode laser beam. In one preferred embodiment, the normal to the bevel is in the plane of the shaped optical element. The bevel is formed by lithographic processing, or the bevel is formed by injection molding. The shaped optical element is reduced in plan area with distance from the bevel.

Preferably, the shaped optical element forms one edge of a flow cell. The sample enters the flow cell and interacts with the fluorophore-polymer film deposited on the shaped optical element. When the sample is a liquid, after filtration it is brought to a vaporization chamber with inlet and outlet valves and a thin film heater. The valves are closed, and the sample is heated within the chamber to vaporization. The valve leading from the vaporization chamber to the flow cell is opened to allow the vapor within the chamber to expand and travel to the location of the fluorophore-polymer film. The vaporization chamber contains a provision for monitoring the sample temperature and pressure. Preferably, the vaporization chamber is less than 10 mm long and less than 500 microns wide and deep. The heating is performed rapidly, and the vaporization product is detected a specified amount of time after sample vaporization.

Preferably, the semiconductor diode laser is modulated. Preferably, the modulation frequency is 1 kHz. The output of the semiconductor laser is passed through a beam-splitter or line generator or holographic beam splitter. The beam is split into several nearly equal beams.

Preferably, the photodetector is a photodiode with an integrated amplifier. The photodetector output is a voltage. Preferably, there are two or more photodetectors, and at least one of the photodetectors is used to monitor the fluorescence from a reference segment of the shaped optical element. The reference segment of the shaped optical element is coated to protect the fluorophore-polymer film from interaction with the analyte. Preferably, there are two or more photodetectors used to monitor the output from analyte-sensitive segments of the shaped optical element. The voltage output is used as the input to a lock-in amplifier. A Stanford Research Model 510 may be used as the lock-in amplifier.

Preferably, more than one photodiode is used. The light passing within the shaped optical element is visible at the surface of the shaped optical element at a number of discrete bounces. Preferably, the fluorophore is contained within a polymer matrix. The fluorophore/polymer probe is drop cast onto the shaped optical element. The volume drop cast onto the probe surface is in the 75 µl to 200 µl range. The photodiode is covered with an optical filter to restrict light at the excitation wavelength. Preferably, the optical filter is a holographic filter. The input sample may be a liquid. The flow cell is protected to allow liquid flow.

The sample may be evaluated by immunological methods as well as by optical fluorescence based methods. The sample may be input through a grooved sheet of plastic formed over the shaped optical element.

The new modular probe provides a continuous monitor based on total internal reflectance spectroscopy. An internal reference removes effects of temperature, film age, et cetera. The invention provides sampling of a liquids stream through vaporization of small volumes of sample material and direction of the vapors through the sensor. Multiple channel detection achieves selectivity through vector addition of the responses of each of the sensor channels. In continuous monitoring, a test material is rotated under a set of seats to provide readily refreshed surfaces for chemical analysis. The use of a minimal volume of polymer-fluorophore drop cast on the sensor surface provides a large increase in system sensitivity.

The current invention uses two or more photodiodes to detect the fluorescence from signal and reference channels. The laser beam is split to provide a reference channel. The shaped optical element is coupled using a bevel of a given angle. An optimum volume for the drop cast solution is presented.

The invention may be used for analysis of chemical warfare agents, toxic gas analysis for industrial health and safety, building air conditioning monitoring, immunological assay, water analysis and industrial process control. The invention provides films with repeatable sensitivity and selectivity, miniaturization and reduction of system costs.

The present invention provides near-infrared excited total internal reflection fluorescence (TIRF) based optical sensors for the detection of chemical threats. The near-infrared-excited fluorescence sensors respond to trace quantities of GD, HD and VX materials, and the response to each material is made selective by selection of fluorophore polymer pairs. A semiconductor diode laser-based sensor detects GD and HD at concentrations less than 0.23 mg/m$^3$ (41 ppb) and VX at concentrations less than 200 ppb. Instrument optimization results in sensitivity to Dimethyl Methylphosphonate (DMMP) at less than 1 ppb. The sensor response time in the presence of GD is approximately one minute. An integrated sensor based on the interaction of the evanescent field of a surface sensitive diode laser waveguide with a chemically sensitive film deposited on the laser surface has sensitivity to DMMP.

The invention provides organic thin films having affinity for agent vapors and the immobilization of fluorescent probes in these thin films to produce a sensitive method of detecting chemical warfare materials. Polymeric materials that adsorb a range of agent materials are used to immobilize semiconductor diode laser-excitable dyes to respond to chemical warfare agents. The combination of thin polymer films with near-infrared excitable dyes for detection of chemical and biological materials is advantageous. The diffusion and reaction zones of a sensor based on a fluorophore immobilized in a polymer matrix reduces dimensions, thereby resulting in rapid sensor response. Organized thin polymer films are compatible with silicon, gallium arsenide, indium phosphide and silicon carbide semiconductor materials, thereby allowing optical integration to a small, rugged sensor package. Near-infrared fluorophores are excited in a wavelength region where there are fewer interferences than observed with excitation in ultraviolet or visible regions of the spectrum. The compatibility of near-infrared fluorophores with semiconductor diode laser excitation improves signal-to-noise ratio with minimal package size. Semiconductor diode lasers are inexpensive, rugged and suitable for field use. Sensors developed based on fluorophores excitable by semiconductor diode lasers are manufactured inexpensively and packaged for portability or for use as an array of point detectors.

Thin fluoropolyol (FP), poly(epichlorohydrin) (PECH), and Nafion films are deposited on beveled glass substrates. The films are deposited with fluorescent materials sensitive to chemical agents and simulants. A wide range of near-infrared fluorophores in the selected polymer thin films are responsive to dimethyl methylphosphonate. FP and PECH thin films are used in conjunction with semiconductor diode lasers to differentiate Soman (GD), VX and Mustard (HD) agents. The sensor response time to GD is approximately one minute. The sensor is reversible to GD in that removal of the chemical agent results in return to the original fluorescence level in about one minute.

A chemical sensor based on a semiconductor surface sensitive diode laser (SSDL) has the ability to detect DMMP at 200 ppm levels through interaction of the evanescent field of the diode laser waveguide with a chemically sensitive film deposited on the laser surface.

These and further and other objects and features of the invention are apparent in the disclosure, which includes the above and ongoing written specification, with the claims and the drawings.

DETAILED DESCRIPTION OF THE PREFERRED EMBODIMENTS

The invention provides sensitive, selective and stable chemical and biological sensors for use in defense and commercial applications, including decontamination and demilitarization.

TIRF miniaturized instrumentation and thin film sensors are used to evaluate chemical warfare materials. The miniaturization and improved sensitivity of a diode laser-based TIRF detector and the selection polymeric derived thin film layers for immobilization of selective fluorophores provides rapid identification of chemical or biological threats.

Needs exist for low-cost sensors exhibiting rapid response at very low concentrations of chemical warfare agents. The total internal reflection fluorescence instrument has been improved through substitution of an external lock-in amplifier for the HP-4194 test box used in previous work. The application of an amplified photodiode in the test instrument provided further miniaturization of the sensor system. Beveled glass slides are used rather than a prism coupling to excite fluorescence. Polymer and fluorophore combinations capable of ameliorating present limitations in instrument response times at low agent concentrations have been identified. Several polymers as an immobilization matrix for near-infrared excited fluorescent dyes provide sufficiently rapid response to allow real-time detection of these materials. Selective responses to GD, VX and HD using polymers having differing solvation parameters have been provided.

Figure 1:
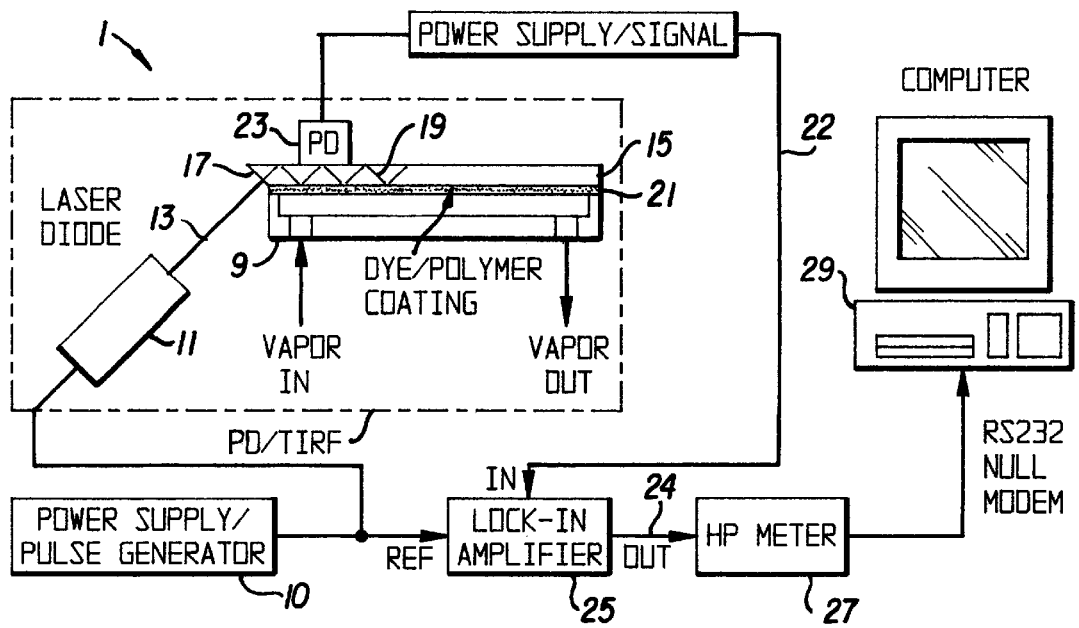
FIG. 1 shows a setup for detection of chemical vapors using a photodiode/amplifier (PD).

Based on the design of a previous total internal reflection fluorescence (TIRF) setup (Groger et al., 1995), a new opto-mechanical device is provided. The new device incorporates a number of technical advancements to reduce the size, weight and cost, while maintaining the sensitivity of the original prototype. A simplified functional block diagram of the new TIRF 1 setup is shown in FIG. 1. A power supply and pulsed generator 10 supplies 1 kHz square wave pulses to the laser diode 11 and a reference signal to lock-in amplifier 25. The excitation is provided by a focusable visible laser diode module 11 emitting at 635 nm (Thorlabs Model 0220-843-00). The theoretical output power of the laser diode 11 is 2.5 mW in continuous wave excitation, and an average output power is 1.6 mW under 1 kilohertz square wave modulation. The laser output 13 is focused into a glass slide 15 having a 65° bevel angle 17. The focal point of the laser assembly is approximately 10 cm away from the laser. The laser beam 13 undergoes total internal reflection 19 inside the beveled glass slide 15 and at the even numbers of reflections excites a thin layer 21 of dye-doped polymer. The fluorescence 20, shown in FIG. 2, emitted from the polymer layer 21 is collected by a photodiode/amplifier package 23 (Burr-Brown OPT301). The fluorescence signal 22 is demodulated and further amplified by a lock-in amplifier 25 (Thorlabs Model LIA100 or Stanford Research Systems Model SR510) and the DC signal 24 is measured and transferred by a digital voltmeter 27 (Hewlett-Packard Model HP 34420A or Pico Technology Model Pico ADC-16) to a computer 29 for recording and charting.

The new modular flowcell 9 is amenable to rapid replacement of a dye/polymer coated slide 15. The new flowcell 9 also reduces labor in optical alignment.

A 65° beveled slide 15 was used as a substrate for the dye/polymer 21, as well as the medium for evanescent excitation of the dye via total internal reflection.

A new integrated laser diode 11 was used, which has automatic optical power control that provides a stable optical source for fluorescence measurement.

Figure 29:
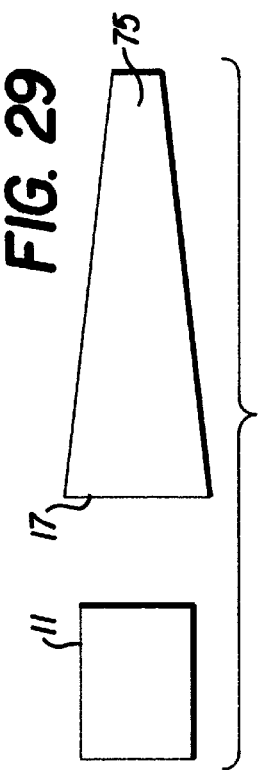
FIG. 29 is a top view of a shaped optical element that has a decreasing plan area as the distance from the beveled edge increases.
Figure 28:
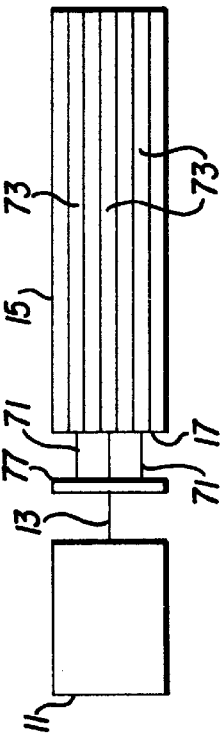
FIG. 28 is a bottom view of the shaped optical element with a plurality of fluorophore stripes for detecting multiple analytes.
Figure 4:
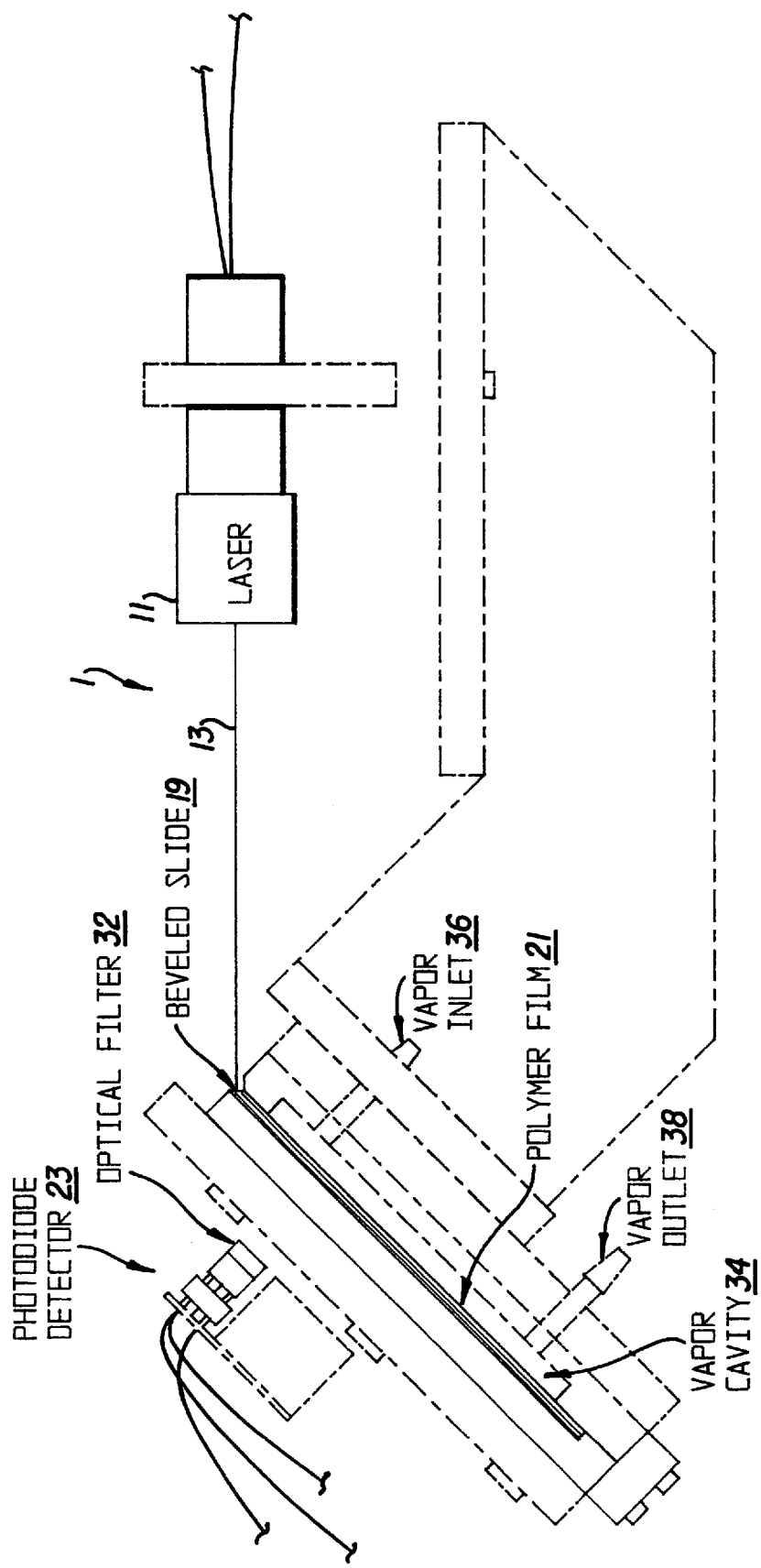
FIG. 4 is a front elevation of a flowcell for detection of DMMP.
Figure 5:
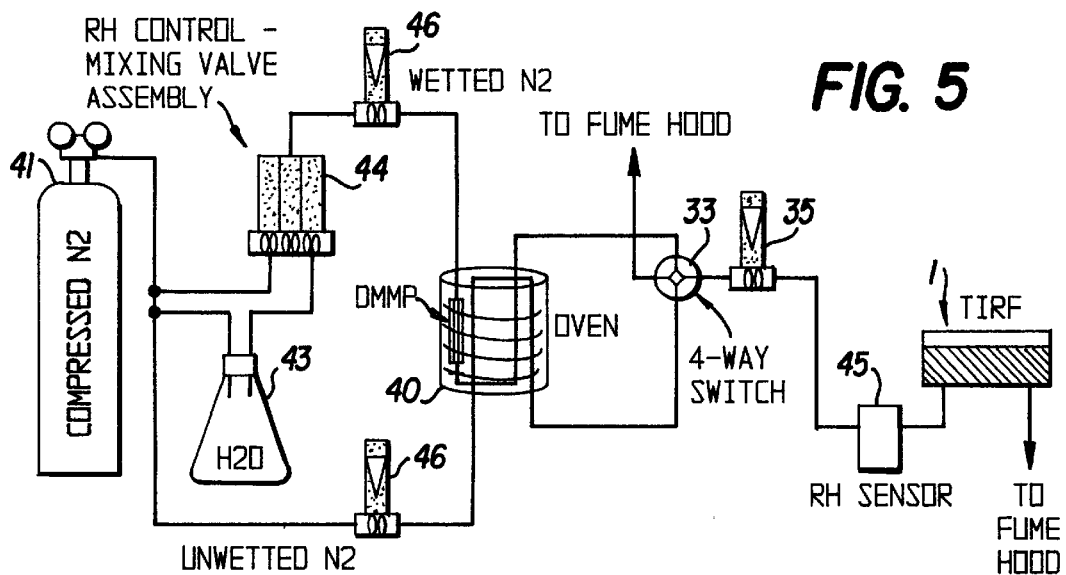
FIG. 5 shows a setup for a variable humidity generator.

The modular probe contains a flow cell used for vapor samples or modified for liquid samples. Fluorophore-polymer volumes drop cast on the surface of the shaped optical element provide unusually high sensitivities when monitored using the lock-in amplifier apparatus. The instrument uses either a beam splitter 77 or line generator after the diode laser 11, as shown in FIG. 28, to spread the laser beam 13 to allow multiple channels of detection. For a 2.54 cm by 7.62 cm shaped optical element, parallel beams 71 would enter at the bevel 17 and travel along the element 15. As an example, along the 2.54 cm length of the bevel plate, as many as eight stripes 73 are formed. These stripes 73 are formed from a range of polymer and fluorophore materials sensitive to each of the analytes of interest. Multiple photodiodes detect the fluorescence from each stripe. Each photodiode is monitored using a digital signal processing apparatus. A digital-signal processing technique is used for low-intensity fluorescence detection. The diode laser is modulated at a frequency from 500 Hz to 5000 Hz. The fluorescence and residue excitation signals are separated and detected as different channels. As shown in FIG. 29, the shaped optical element 15 may reduce in plan area 75 with distance from the bevel 17.

A photodiode 23 is incorporated, which has an integral amplifier package that reduces the size and cost of the prototype and may be used under ambient light.

An inexpensive lock-in amplifier 25 is used to increase the sensor signal-to-noise ratio.

Figure 2:
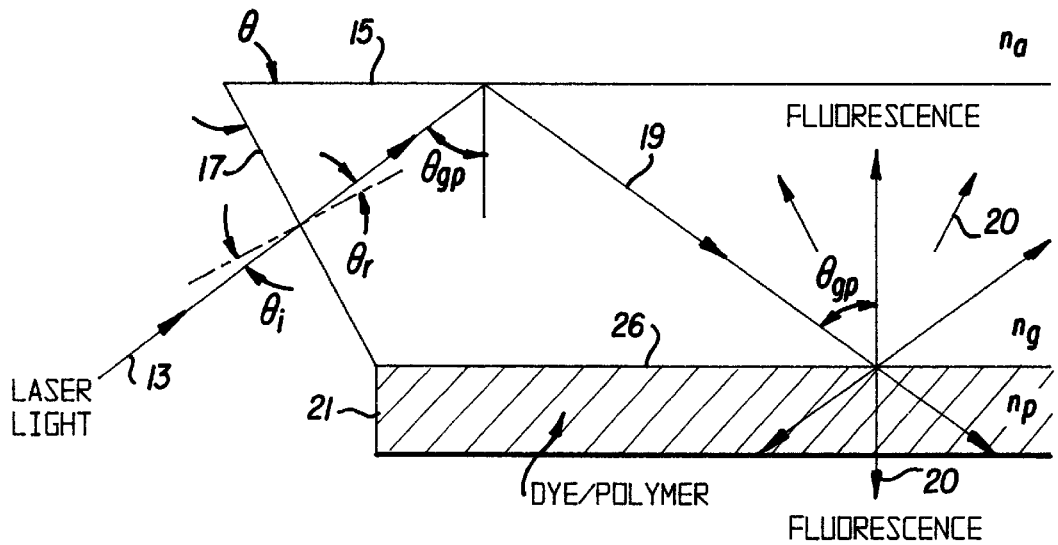
FIG. 2 shows geometry of fluorescence excitation through total internal reflection on a beveled glass substrate.

One of the modifications from the previous total internal reflection fluorescence (TIRF) setup is the use of a beveled glass substrate 15 in place of prism coupling of the laser light 13 into the slide. The beveled edge 17 is polished at a set angle so that the excitation laser beam 13 is coupled into and totally internal reflected at the glass substrate 15. The reflected beam 19 excites the dye-doped polymer thin film 21, and the interaction of the dye/polymer probe with the analyte is monitored through the change in fluorescence of the film. The geometry of fluorescence excitation through total internal reflection is shown in FIG. 2, where e is the bevel angle, $\theta_i$ is the incident angle, $\theta_r$ is the refracted angle, $\theta_{gp}$ is the incident angle at the glass/polymer interface, $n_a$, $n_g$ and $n_p$ are the refractive indexes of air, the glass substrate and the polymer, respectively. Using Snell's law, the incident angle at the glass/polymer interface 26 is related as $$\theta_{gp} = \theta - \sin^{-1}\left(\frac{\sin\theta_i}{n_g}\right) \tag{5}$$

Conditions for total internal reflection at the glass/polymer interface 26 are met when $\theta_{gp}$ is smaller than the critical angle at the interface ($\theta_c = \sin^{-1}(n_p/n_g)$).

Two bevel angles were investigated, 45° and 65°. Experiments were performed to determine the optimum bevel angle and angle of incidence. It was determined that an angle of incidence of $\theta_i=20°$ may be used to balance the Rayleigh scattering signal and the fluorescence signal. Both 45° and 65° bevel slides are custom polished starting from soda lime microscope slides of dimensions 25.4 mm×76.2 mm×1 mm (Gould Precision Optics, Inc., Binghamton, N.Y.). The bevel edge 17 on the substrate 15 is polished to a 60-40 scratch and dig surface finish.

Figure 3:
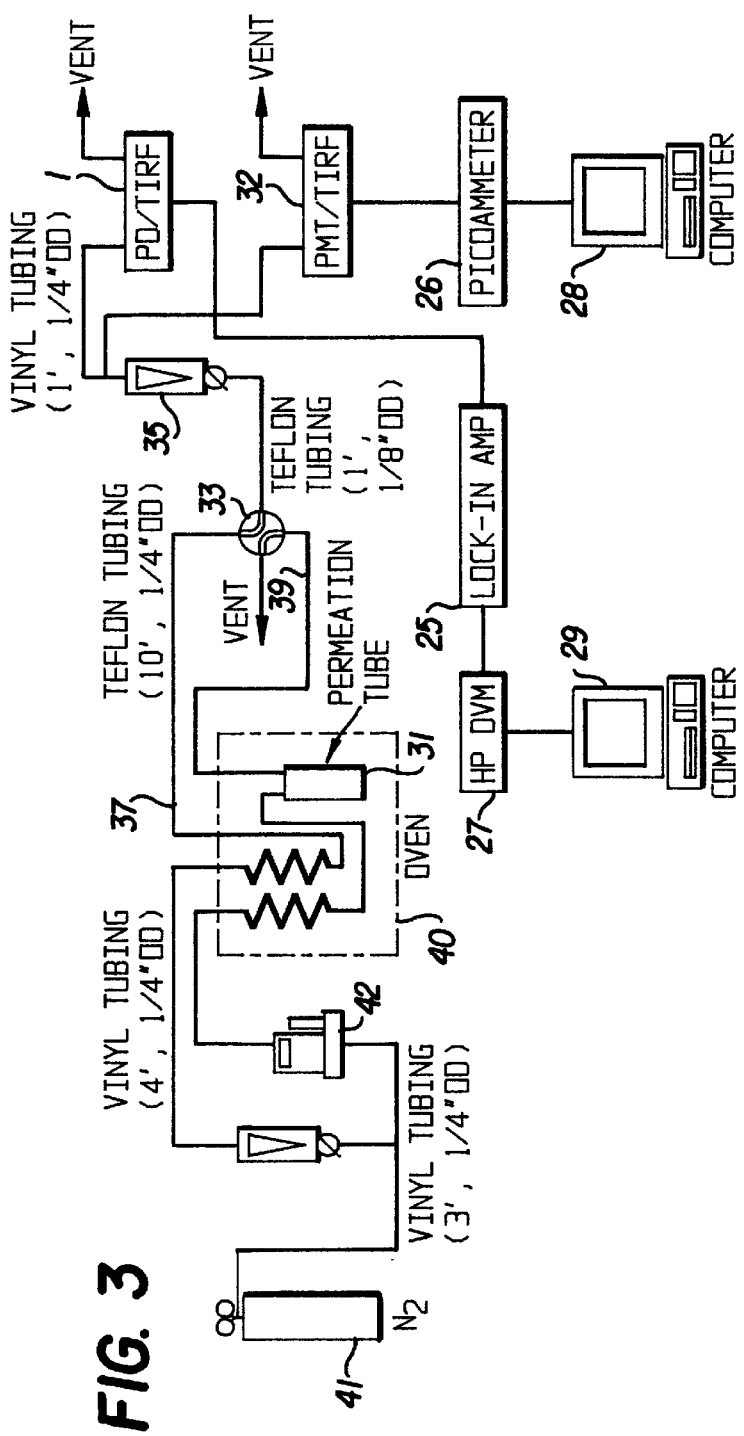
FIG. 3 shows a setup for detection of DMMP vapor.

Differences in sensitivity between the prior TIRF system and the present miniaturized system were evaluated using parallel flow configuration providing identical vapor concentrations to the two experimental instruments. The PMT/TIRF reference measurement was made using a picoammeter 26 and a computer 28. It was observed that the PMT based system 32, as shown in FIG. 3, was amenable to use at low intensity light conditions but not appreciably more sensitive than the photodiode/lock-in amplifier based system 1. Therefore, the TIRF Reference System was not used in further experimentation.

Vapor streams containing reference air and reference air with agent must be equalized with respect to all experimental variables including vapor and probe temperature, relative humidity (water vapor concentration) and flow velocity in order to achieve a repeatable test result.

Prepared fluorophore-polymer coated substrates are used in screening coatings sensitive to chemical warfare agents. During the course of the project, over 120 dye/polymer coated substrates were fabricated. The first step in the deposition process involves thorough cleaning of the substrate surface. The next step involves preparation of dye/polymer solutions to the desired concentrations and deposition onto the cleaned substrates. All the solvents used in the preparation of the fluorophore-polymer probes are reagent grade and used as received. Most of the dye/polymer coatings are deposited using a solution cast method. This method involved measuring a calibrated amount of dye/polymer solution into a micro-pipette and transferring the coating material to the substrate surface so that the solution spreads over the entire substrate surface. The substrate is kept level to ensure a uniform film thickness and is allowed to dry in an open atmosphere. The thickness of the film is controlled by varying the concentration of polymer in the coating solution as well as the volume of the solution used in the casting process. In some cases, particularly with the fluoropolyol polymer, it was observed that a 50% relative humidity or higher influences the formation of a clear film. In this case, the drying and polymerization step is performed in a desiccator under a low vacuum. Table IV tabulates the preparation of representative dye/polymer thin films and the films used for agent testing. See Table XI for acronym and symbol definitions.

The substrate may be cleaned by either a solvent cleaning or acid cleaning method. The solvent cleaning method entails the following steps. First, the glass substrate is washed in glass detergent, then rinsed with de-ionized water. Then the substrate is rinsed with acetone. Then the substrate is cleaned with acetone for five minutes using an ultrasonic bath, followed by a methanol rinse. Then the substrate is cleaned with methanol for five minutes using an ultrasonic bath. The substrate is then dried using nitrogen from a cylinder. Then the substrate is plasma cleaned using a plasma cleaner at full power for three minutes. The deposit dye/polymer film is then immediately applied.

The first step in the acid cleaning method is to clean the substrate using the solvent cleaning steps. Following the solvent cleaning, the substrate is lowered into a heated, concentrated sulfuric acid/hydrogen peroxide (1:2) solution for one minute at 100° C. That procedure removes all the organic residue on the substrate surface. The surface is very hydrophilic after the treatment procedure. The substrate is then dried using nitrogen from a cylinder. The deposit dye/polymer is then immediately applied. The spent acid/peroxide solution is stored in an open glass container to vent the evolved gas.

Optimization of the polymer coating thickness is performed to improve the sensor rise time and sensitivity to agents. A dye/polymer of OX170/FP combination is used for this process. An attempt was made to determine the effects of deposition methods on the sensitivity of fluorophore polymer films. Thin-polymer films were deposited using solvent cast and spin-cast methods. Depositions using different spin rates and multiple layers were attempted. Thin polymer films were deposited over a layer of piezoelectric spacer material, such as lead zirconate titanate (PZT), to determine the effect of the use of high refractive index coatings on instrument sensitivity. Table V tabulates the fabrication parameters for some dye/polymer thin films for the optimization process. All of the bevel glass substrates were cleaned using a solvent cleaning procedure. The dye/polymer solvent was ethanol. Concentrations of $10^{-5}$M/0.48 wt % and $10^{-5}$M/0.48 wt % were used on substrates 970513A-1 and substrates 970521A-C, respectively.

The experimental setup for detection of DMMP in the vapor phase included a means of generating a calibrated amount of vapor together with gas delivery and mixing systems for vapor phase chemical detection. The experiment setup for generation and detection of a calibrated DMMP vapor is shown in FIG. 3. A gas permeation tube 31 generates calibrated concentrations of DMMP for sensor evaluation. Both refillable and Trace-Source disposable DMMP permeation tubes (Kin-Tek Laboratories, LaMarque, Tex.; Model LFHA-2000.00-5017 and HRT010.005017/100) are integrated with a flowcell to provide DMMP vapor generation at predictable flow rates and concentrations. A refillable permeation tube provides DMMP in the concentration range from 100 ppb to 100 ppm, whereas a disposable tube provides concentrations from 1 ppb to 1 ppm. The design of the flowcell 1 and the arrangement of the laser diode 11 is shown in FIG. 4. Note that the laser beam 13 is aligned with the glass substrate 19 at an angle of 45° along the edge, and that a 65° beveled angle substrate is used. Using an incident angle of $\theta_i$=20° to the beveled edge and a glass refractive index of 1.5, the incident angle, $\theta_{gp}$, at the polymer/glass interface is computed to be 52° with respect to the normal. That arrangement is shown to provide good penetration depth for the evanescent wave and reduced scattering noise. An optical filter 32 is used on the photodiode detector 23. Vapor cavity 34 has a thickness similar to the thickness of the slide plate 19. A vapor inlet 36 flows vapor into the cavity 34 and a vapor outlet 36 conducts the vapor out of the cavity.

Referring to FIG. 3, a mass flowmeter 35 downstream of the 4-way valve 33 is used to measure the flow rate through the sensor and to control a flow controller 42 to balance the flow for the nitrogen 37 and the DMMP vapor streams from the heater oven 40. A nitrogen source 41 supplies nitrogen to line 37 and to the flow controller 42.

A variable humidity setup provides a controlled stream of humid nitrogen laden with DMMP. A schematic of the setup is shown in FIG. 5. The humidity is added by passing the $N_2$ gas 41 through a 250 ml Erlenmeyer flask 43 filled to 100 ml with water. The humidified $N_2$ then goes into a mixing valve assembly 44 having two inputs and a common output; dry $N_2$ is added to the second input. Flowmeters 35 and 46 measure flows. Four-way valve 33 selects flow. A humidity sensor 45 is also incorporated into the system. The sensor was removed from the inside of a Fisherbrand Monitoring Thermometer/Humidity Sensor and inserted into a small glass vial (approximately 18 cm$^3$) through which the $N_2$ gas flows. The vial is located just before where the $N_2$ enters the flowcell assembly. The pure dry $N_2$ is measured to have a range from 8–11% relative humidity, and the pure humidified $N_2$ ranges from 37–40% relative humidity. The 8% measured relative humidity for dry nitrogen is probably due to inability of the humidity sensor to monitor such a low humidity, and thus should be reading as 0%. As a result, the range of humidity may be varied from approximately 0–40%.

An experiment was performed to determine the feasibility of detecting the chemical warfare simulant, DMMP, under water. The experiment employed the fluorophore-polymer film found to be most sensitive in vapor-phase detection experiments. This film comprised Oxazine 170 as the fluorophore and fluoropolyol as the polymer. The film was prepared with a water protective layer as an overcoat. It was the hypothesis that some of the DMMP will transverse through the gas permeable layer and interact with the fluorophore-polymer film. A solution was prepared having 0.5 wt % fluoropolyol and $10^{-5}$ M Oxazine 170. A volume of 43 µl of this dye/polymer solution was deposited on microscope slides of dimensions 19.5 mm×38.5 mm. Coatings were prepared containing only the fluorophore-polymer pair (Type A), the fluorophore polymer film overlaid with a layer of TEFLON AF (Type B), and the fluorophore-polymer films covered with, a thin sheet of TEFLON (Type C). The TEFLON AF coating was applied by immersion of the polymer coated substrate into a 1% TEFLON AF solution (E. I. Du Pont De Nemours & Co., Wilmington, Del.), and then withdrawn from the solution at the rate of approximately 2.5 cm/s.

Figure 6:
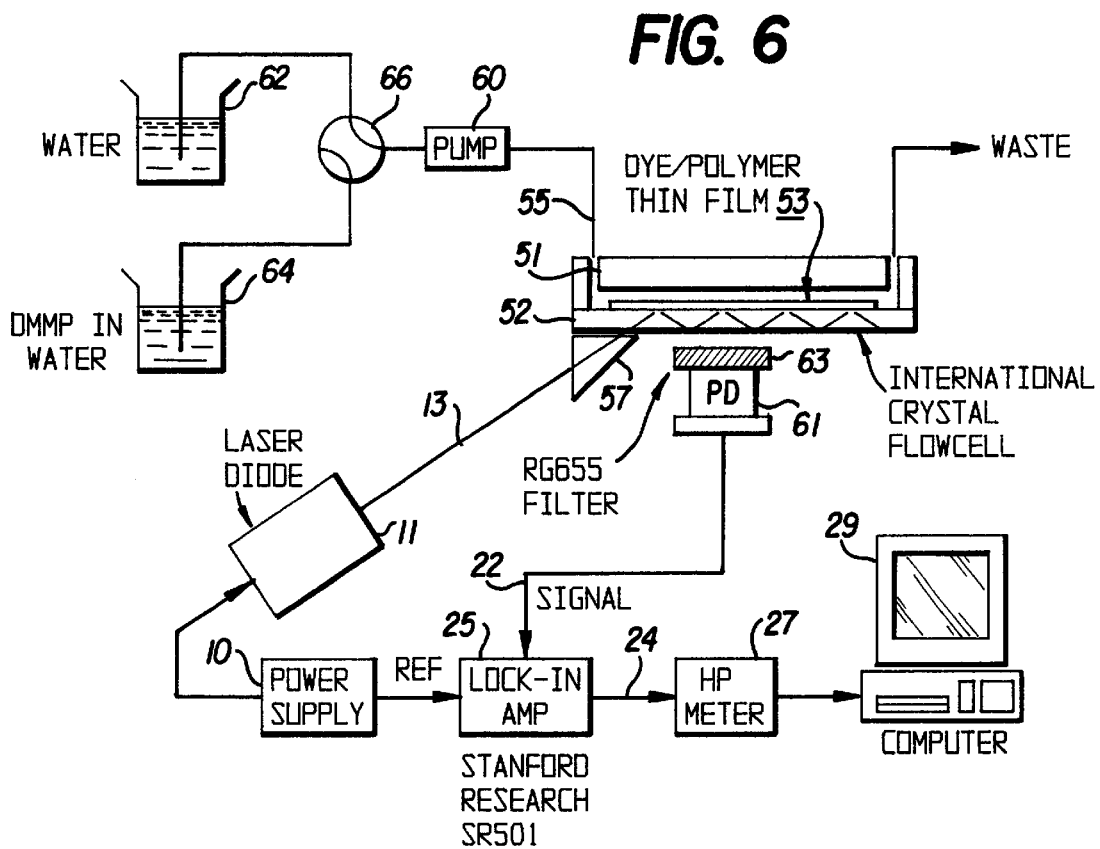
FIG. 6 shows a setup for detection of DMMP in water.

An experimental set up based on a previous program (Groger et al., 1995) was modified for use in this part of the program. A schematic of the set up is shown in FIG. 6. The flowcell consists of an infrared transmission cell 51 (International Crystal Lab., Garfield, N.J., Catalog No. 0006-497) that was modified to allow the fluorophore-polymer film 53 to come into contact with DMMP solution 55. A 90° prism 57 (Edmund Scientific, Part Number A45, 106) was used to couple the laser light 13 into the glass slide 52. A photodiode/amplifier package 61 having a 655 nm long-wave-pass filter 63 was used to detect the change in fluorescence. The electronic portion of the experimental setup was identical to that used for detection of DMMP in vapor phase. A pump 60 drew water from a pure water source 62 or a DMMP water solution 69 as controlled by a four way valve 66.

Figure 7:
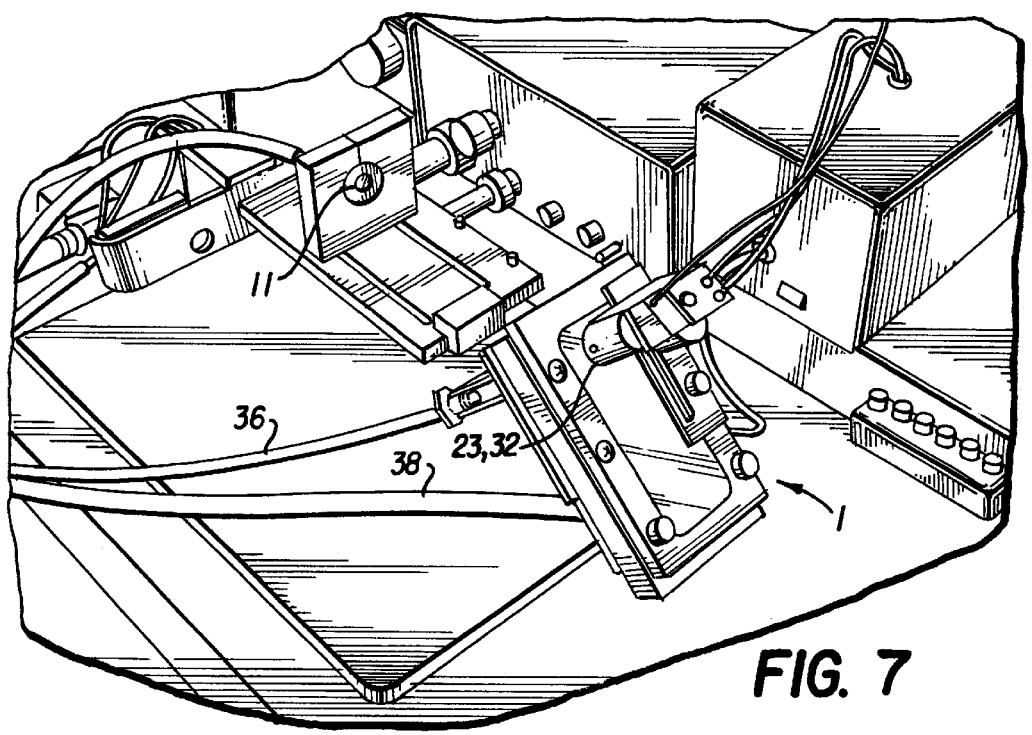
FIG. 7 is a perspective view of a setup for detection of vapor phase DMMP.
Figure 8:
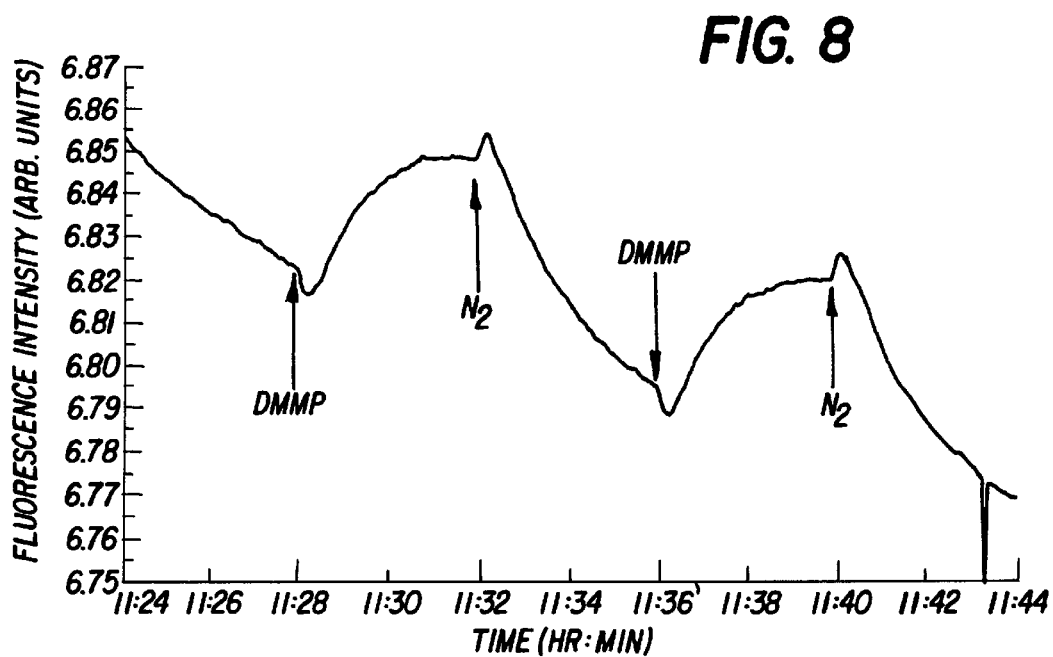
FIG. 8 is a graph of the response of OX170/Fluoropolyol film to 3.2 ppb of vapor phase DMMP.
Figure 9:
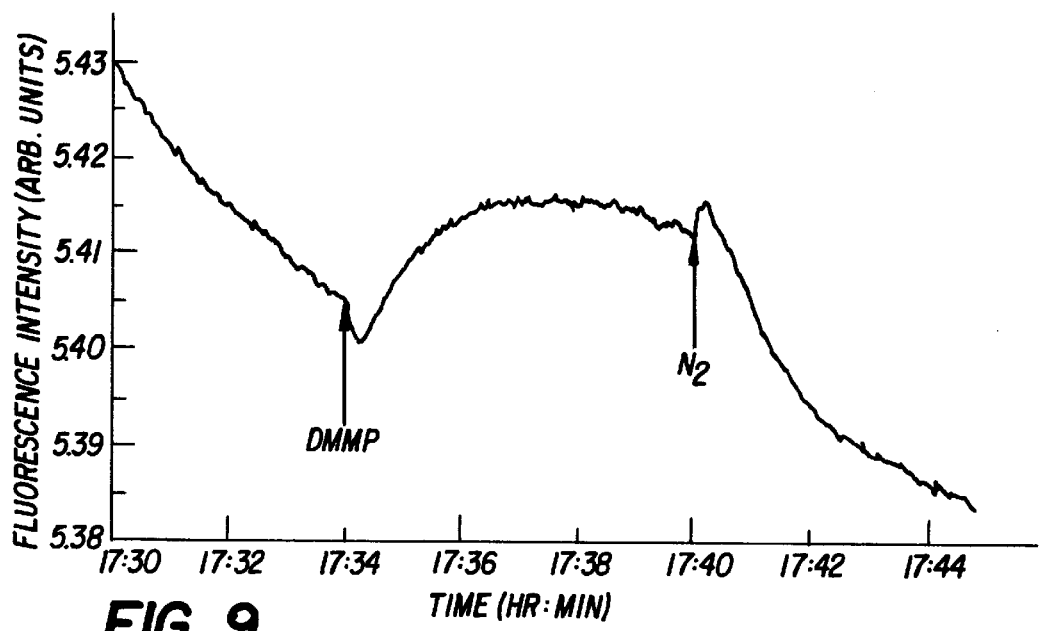
FIG. 9 is a graph of the response of OX170/Fluoropolyol film to 1.2 ppb of vapor phase DMMP.

A number of dye/polymer thin film combinations were fabricated and tested using an experimental setup as shown in FIG. 7. Table VI tabulates the dye/polymer combinations tested during the program. Table VII tabulates the estimated sensitivity towards DMMP at the present form. Further improvement in sensitivity may be obtained on each film if its film thickness and dye concentration are optimized. It was observed that the OX170/Fluoropolyol (OX170/FP) film has the highest sensitivity of films tested to date towards DMMP. FIGS. 8 and 9 show the responses of an OX170/FP film (Film number: 970521A) to 3.2 ppb and 1.2 ppb of DMMP in vapor phase, respectively. That low concentration of DMMP vapor was generated using a flow rate of approximately 400 mL/min of nitrogen gas, and the disposable permeation tube was kept at 34° C. and 23° C. for 3.2 ppb and 1.2 ppb DMMP, respectively. To detect DMMP at this concentration, a more expensive lock-in amplifier (Stanford Research Systems Model SR510) has been used. It may be noted that the signal-to-noise ratios shown in FIGS. 7 and 8 are substantial, suggesting lower limits of detection may be observed for laboratory arrangements capable of generating lower concentrations of challenge vapor. Further reduction in the detection limits for DMMP may be obtained using a low noise photodiode/amplifier package or an integrated avalanche photodiode in conjunction with a digital lock-in amplifier such as Stanford Research Systems Model SR850.

Figure 10:
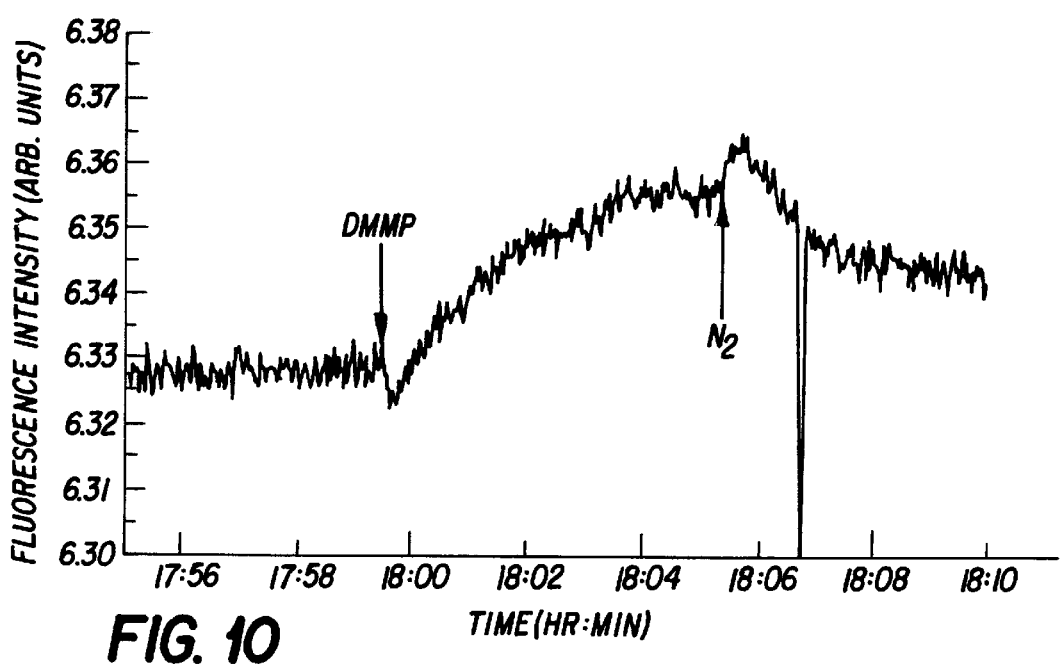
FIG. 10 is a graph of the response of OX170/Fluoropolyol film to 1.2 ppb of vapor phase DMMP with a neutral density filter installed.

Also noted in FIGS. 8 and 9 is the presence of instrumental drift in the sensor system. Experiments were carried out to determine methods to eliminate drift in the TIRF system. An experiment was performed using OX170/FP as the probe ($10^{-5}$M/0.48 wt %, 100 µl deposited on slide). The films were exposed to 1.2 ppb of DMMP. The TIRF instrument responded to the challenge with a significant fluorescence signal imposed over a downward drift. The drift is consistent with all our experimental observations on the TIRF. When the intensity of the excitation laser light was reduced by a factor of 10 using a neutral density filter, the drift was eliminated. FIG. 10 shows the sensor response to 1.2 ppb of DMMP with the neutral density filter installed. The sensor responded in much the same way as with higher laser intensity although the baseline was somewhat shifted. This experiment shows that the drift may depend on the excitation laser intensity. Several previous experiments also indicated that the drift may be dependent on the flow rate of the carrier air. A larger flow rate results in larger drift. From these two pieces of information, one may develop the hypothesis that the drift is due to the increase in non-radiative relaxation of the electrons of the fluorophore in the excited state. The drift may be a thermal effect.

The fluorescent dye absorbs the laser light and some electrons are promoted to the excited state. The electrons relax to the ground state via either a radiative or a non-radiative route. The electrons relax to the ground state via the radiative route by emitting a photon at a longer wavelength. Non-radiative relaxation results in an increase of temperature of the fluorophore-polymer coating. When the fluorescent dye molecules are illuminated, the polymer is heated. The increase in temperature increases the percentage of excited electrons relaxing through the non-radiative route, and decreases the fraction of electrons relaxing through the radiative route. As a result, the fluorescence is decreased.

A series of tests were conducted to determine how humidity affects the sensitivity of Oxazine 170-fluoropolyol to DMMP. Tests were run at a range of DMMP concentrations in the presence of $N_2$ at a range of relative humidities. The presence of humidity did not significantly affect the sensitivity of the film to DMMP. In other words, if the relative humidity in a stream of $N_2$ is constant, the response of the sensing film remains the same independent of the relative humidity of the stream. However, the relative humidity was found to proportionately effect the amplitude of the fluorescence of the probe. Tests were conducted at 0, 25 and 40% relative humidities to determine the effect on the fluorescence intensity. No DMMP was used in this test. The set up was altered so that a 4-way switch could be used to quickly switch between dry and humidified $N_2$. The pure humidified $N_2$ (40% relative humidity) increased the fluorescence intensity significantly relative to the dry $N_2$ (8% relative humidity). A mix of dry and humidified $N_2$ was then used along with pure $N_2$ to determine whether the change in fluorescence was related to the relative humidity. The $N_2$ mixture was adjusted to obtain 23% relative humidity, resulting in a humidity difference of 15% compared to the dry $N_2$ (8% relative humidity). This humidity difference is approximately half the difference of 32% used in the previous test. The lower humidity difference decreased the change in fluorescence of the probe by about one half.

A range of dye/polymer thin film combinations were exposed to chemical warfare agents such as GB, GD, HD and VX to evaluate sensitivity, reversibility and response time. Several films were tested for response to the agents GD, VX and HD.

Figure 11:
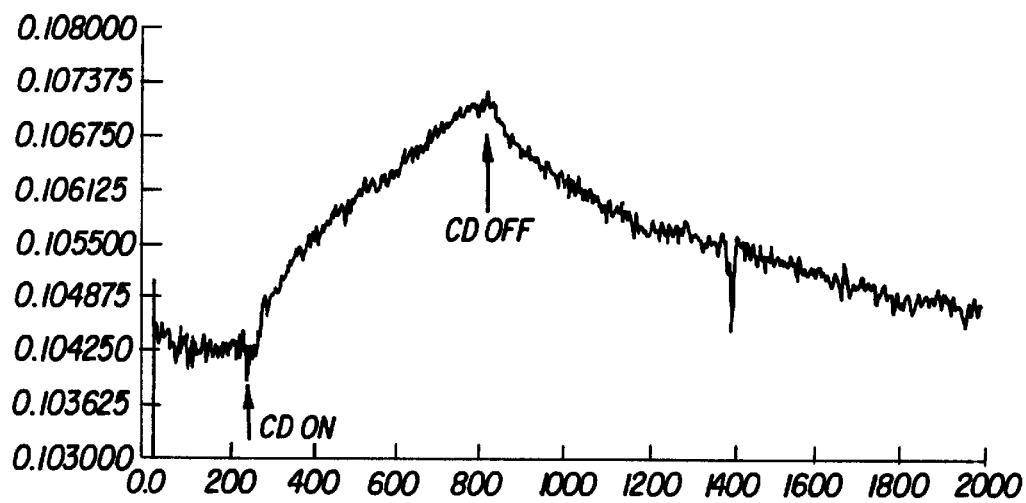
FIG. 11 is a graph of the response of Oxazine 170/Fluoropolyol film to GD at 520 ppb.
Figure 12:
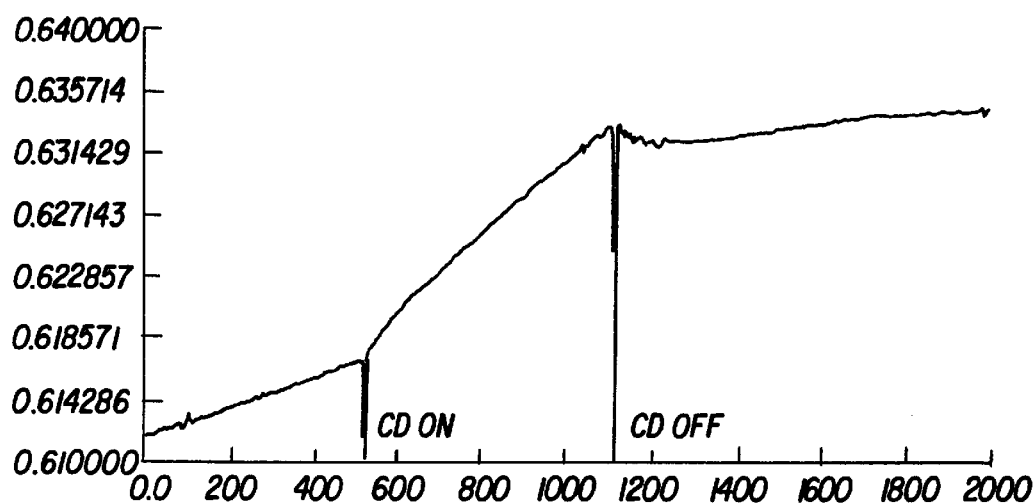
FIG. 12 is a graph of the response of Oxazine 170/Fluoropolyol film to GD at 41 ppb.

A film of Oxazine 170 in Fluoropolyol (FP in Table II) was found to be the most sensitive of those tested to GD. GD was shown to increase the intensity of Oxazine 170 fluorescence as shown in FIGS. 11 and 12 at concentrations down to 41 ppb. Two factors are involved in increasing the intensity of the fluorescence. First, any analyte requires more time to diffuse into the sensitive region (defined by the penetration depth of the evanescent wave and largely independent of overall film thickness) of a thicker film, since a greater distance must be traversed. Second, the GD molecule is heavier and bulkier than the GB molecule and is expected to diffuse more slowly than GB through any polymer film.

Figure 13:
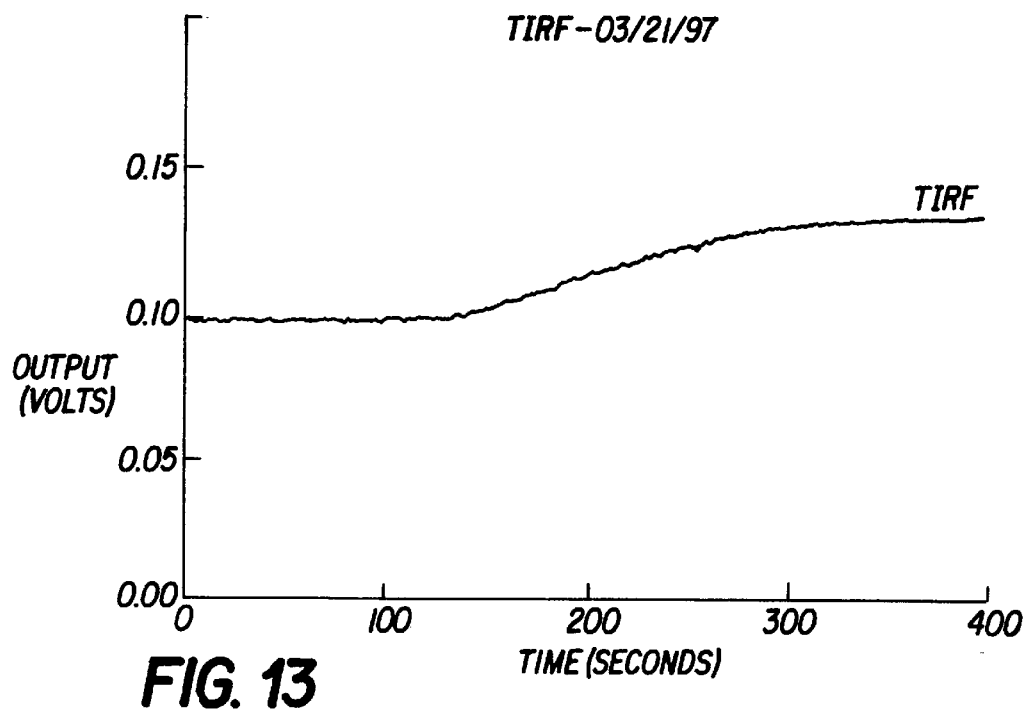
FIG. 13 is a graph of the response of Oxazine 170/Fluoropolyol film to VX at 218 ppb.
Figure 14:
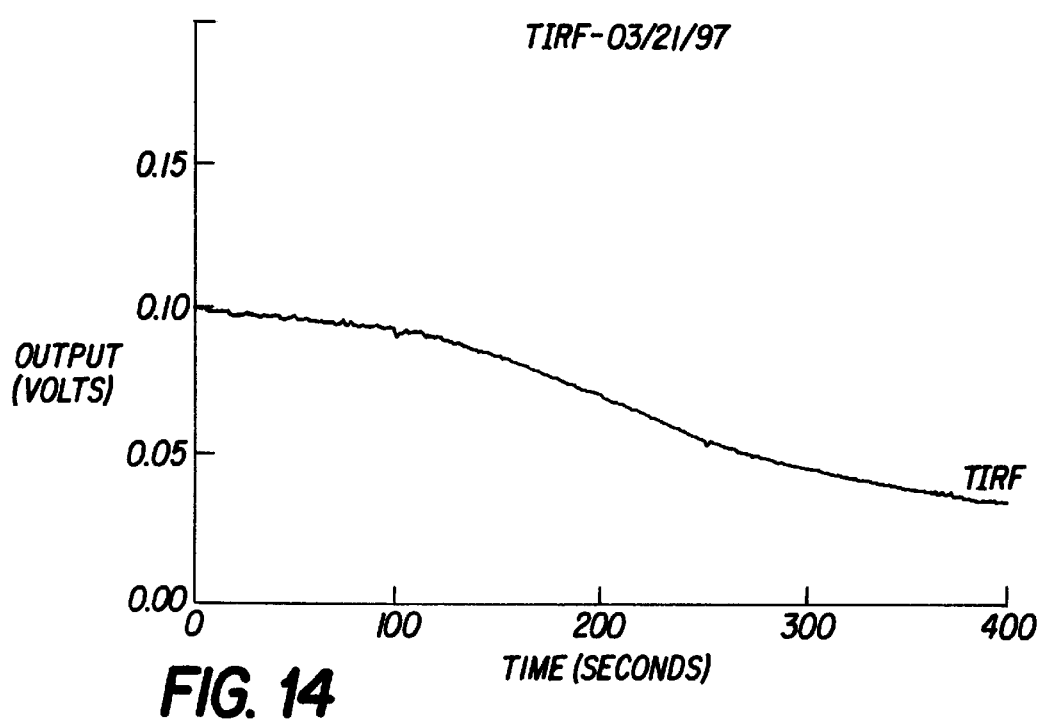
FIG. 14 is a graph of the response of Nile Red/Fluoropolyol film to VX at 209 ppb.

Two films were found to be sensitive to VX. The first, Oxazine 170/Fluoropolyol, exhibited increased fluorescence when exposed to VX at 218 ppb, as shown in FIG. 13. The onset of response occurs within 40 seconds; cleardown is not obtained on the time scale of the experiment. The sense of the response, fluorescence intensity increase, is the same as for GD. The second film, Nile Red/Fluoropolyol, responds in the opposite sense, exhibiting a decrease in fluorescence intensity as shown in FIG. 14. Here, the onset of response is again within 40 seconds and cleardown is not obtained. The films tested were relatively thick, having been made by drop-casting; thus, as alluded to in the above comparison of GB and GD, if the response time is governed by the diffusion rate of the analyte into the film, the relatively slow response to the heavy VX molecule is not surprising.

Figure 15:
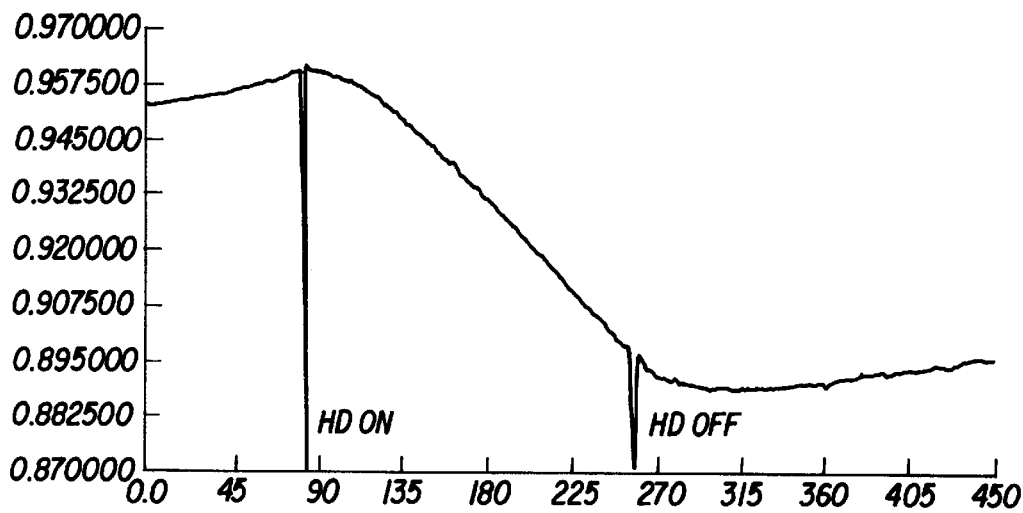
FIG. 15 is a graph of the response of Nile Blue/PECH film to HD at 608 ppb.
Figure 16:
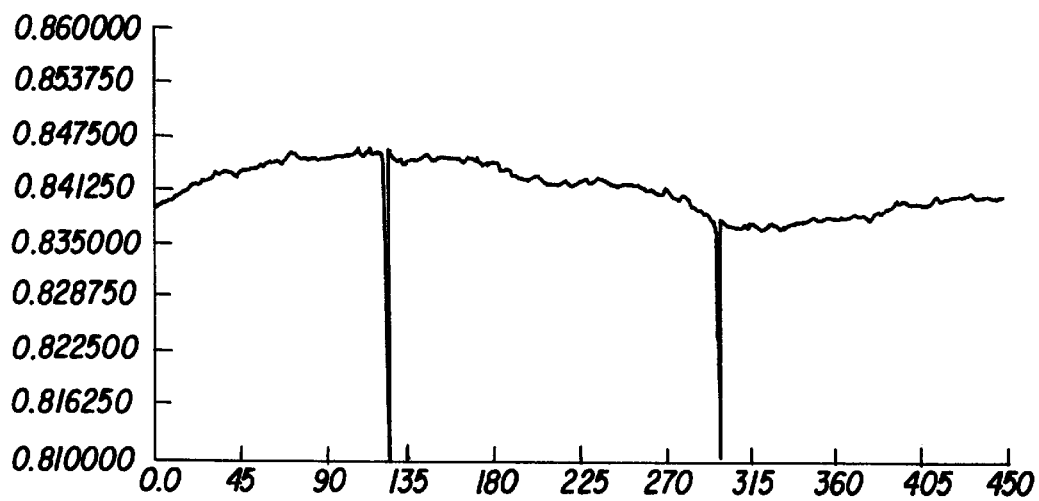
FIG. 16 is a graph of the response of Nile Blue/PECH film to HD at <25 ppb.
Figure 17A:
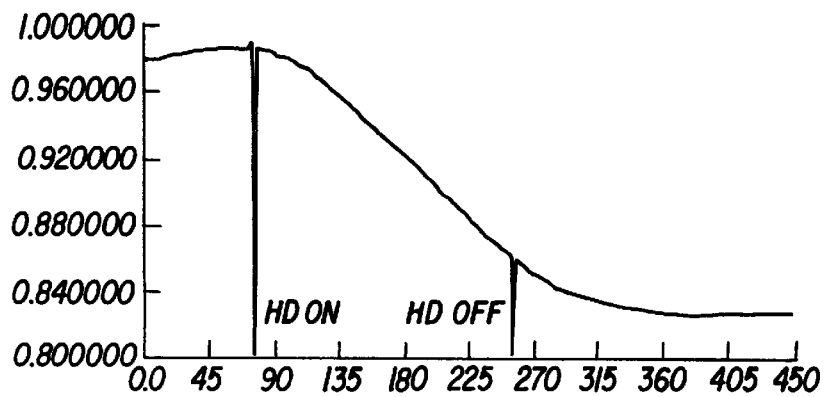
FIGS. 17A, 17B and 17C are graphs of the response of Nile Blue/PECH film to 350 ppb HD, to 166 ppb GD, and reexposure to 243 ppb HD, respectively.
Figure 17B:
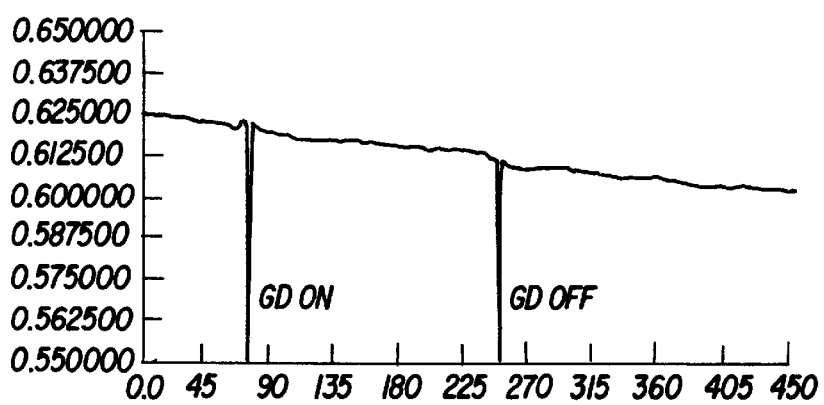
Figure 17C:
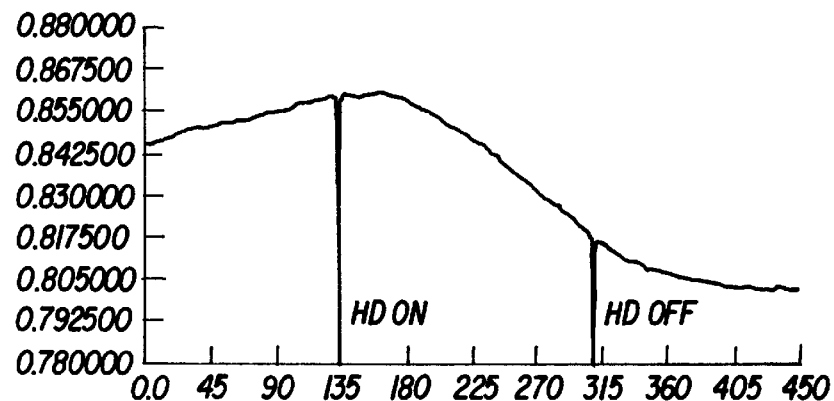

A film of the polymer PECH containing Nile Blue was shown to be sensitive to HD in concentrations down to about 25 ppb, as shown in FIGS. 15, 16 and 17A. In a subsequent test to assess selectivity, the same film was then exposed to GD with no response, FIG. 17B, and then re-exposed to the same concentration of HD, FIG. 17C, with essentially the same response as before the exposure to GD. This behavior is illustrated in FIGS. 17A, 17B and 17C.

Note that the basis for agent selectivity and identification by interpretation of the differential responses of multiple films is contained in the test results obtained to date. The fluorescence of $DiIC_1(5)$ in Nafion decreased upon exposure to GB but, increased upon exposure to DMMP (Groger, et al., 1995). A $DiIC_1(5)$/Nafion film, similar to that previously shown to have high sensitivity to GB, exhibited no response to GD. Instead, Oxazine 170/Fluoropolyol provided the best response of those probes exposed to GD. Nile Blue/PECH responded well to HD but did not respond to GD. Oxazine 170/Fluoropolyol responded to VX in a manner similar to that produced by GD but opposite to the response of Nile Red/Fluoropolyol. Thus, a multiple film probe carrying just the four films discussed in this paragraph can provide a detector capable of distinguishing between GB, GD, VX and HD at concentrations of the order of 100 ppb. These results are summarized in Table VIII.

Figure 18:
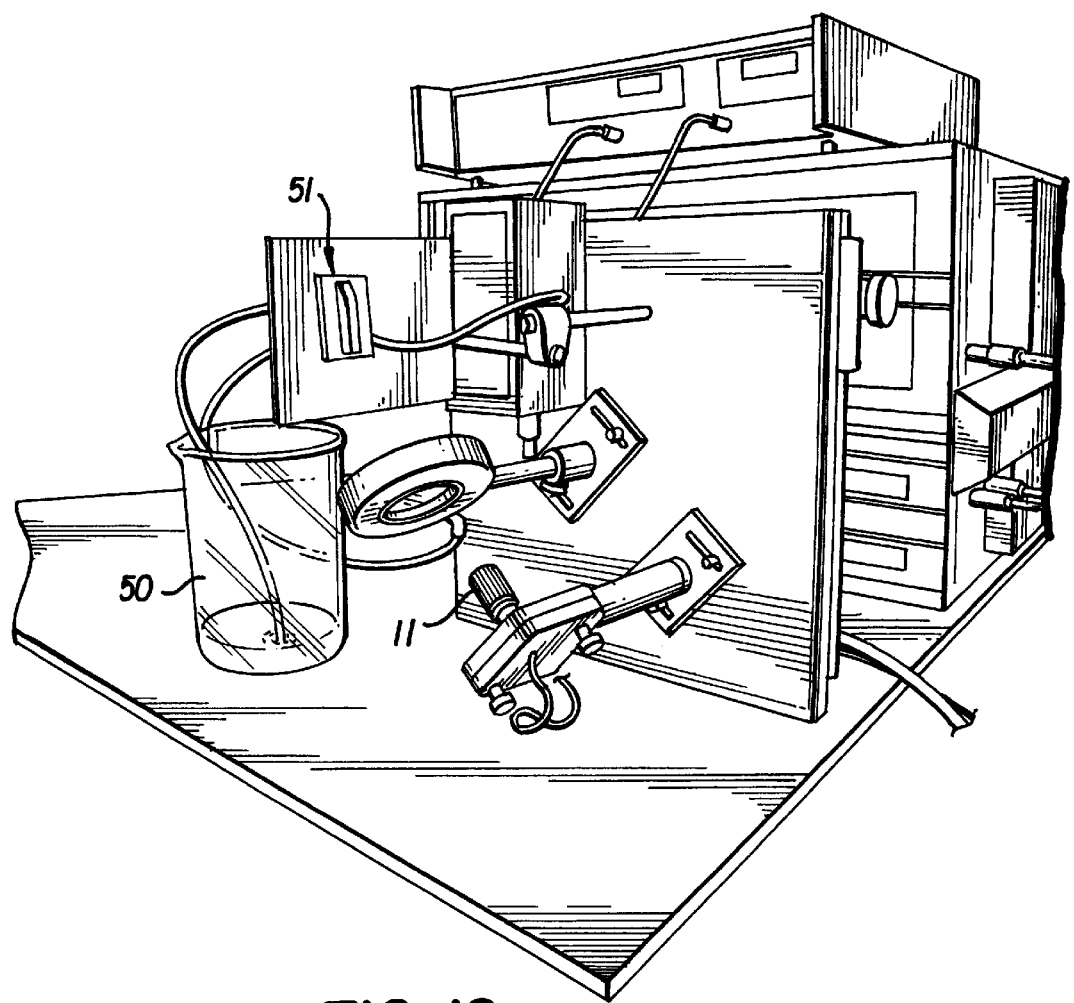
FIG. 18 is a perspective view of a setup for detection of liquid phase DMMP.

A series of tests were conducted to determine the detectability of DMMP in water. Coatings were prepared containing only the fluorophore-polymer pair (Type A), the fluorophore polymer film overlaid with a layer of TEFLON AF (Type B), and the fluorophore-polymer films covered with a thin sheet of TEFLON (Type C). A flowcell was used to allow flow of liquid or gas by the coated plate (see FIG. 18). Initially, vapor phase DMMP was passed through the flowcell to ensure the sensor responded consistently-with previous vapor phase test results. The vapor phase DMMP was detectable with these plates, but the sensitivity was decreased significantly. To eliminate the possibility of DMMP hydrolysis, new solutions were made prior to each test.

Figure 19:
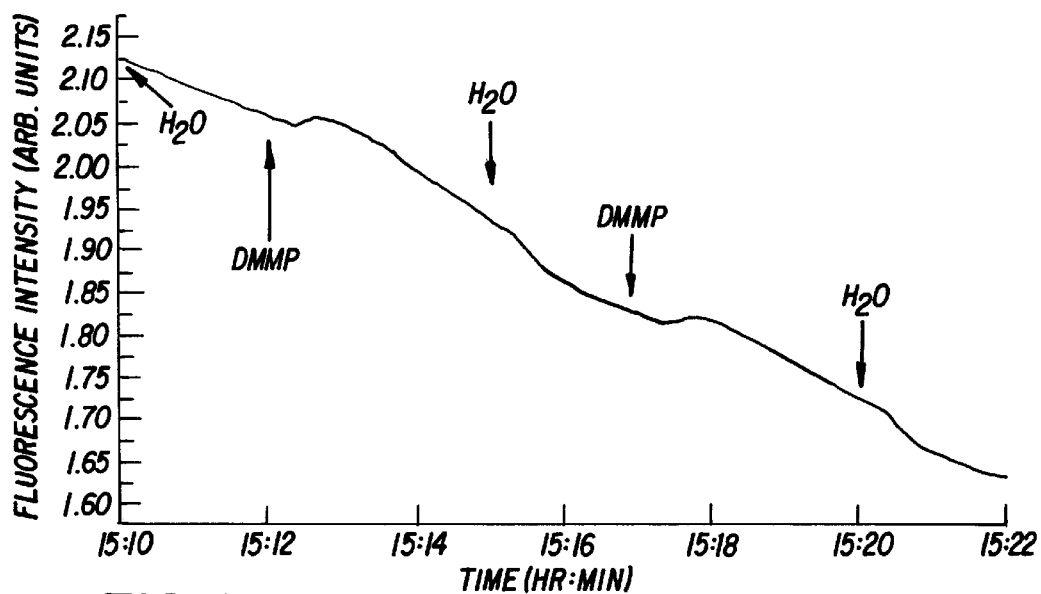
FIG. 19 is a graph of the response of OX170/FP to 2 $\mu$l/ml DMMP in water.
Figure 20:
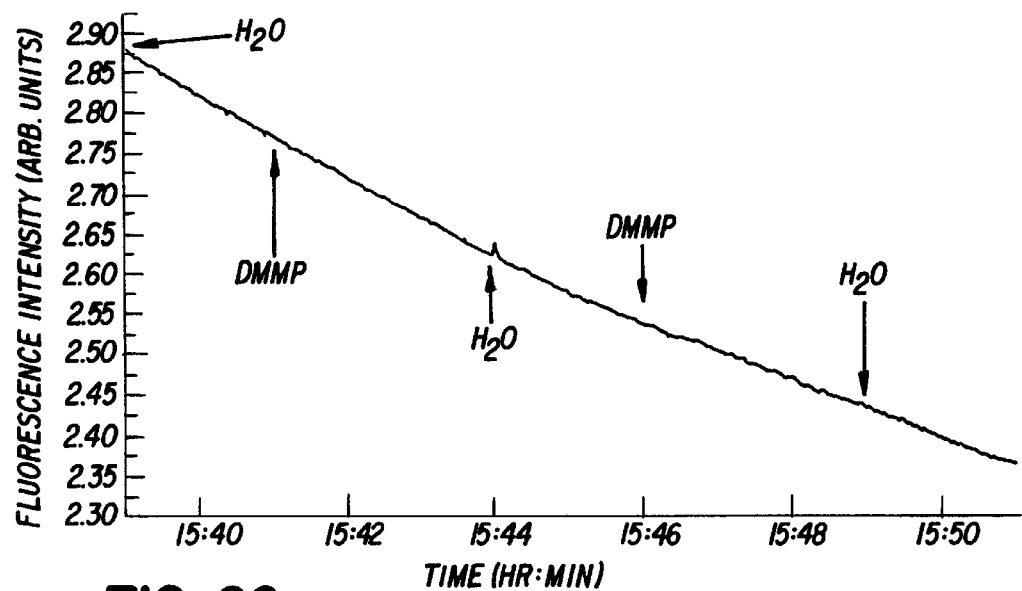
FIG. 20 is a graph of the response of OX170/FP to 0.2 $\mu$l/ml DMMP in water.

FIGS. 19 and 20 show the response of the Type A film (no coating) to DMMP in water at a concentration of 2 $\mu l$ of DMMP in 1 mL of water and 0.2 $\mu l$/ml of water. It was observed that the response time is approximately 30 seconds. Continued drifting of fluorescence signals made it hard to determine the limit of detection. After subtracting a straight line from FIG. 20, a detection limit of approximately 0.2 $\mu l$/ml (SNR of 2) of water is deduced. The drifting is probably due to swelling of the polymer under water.

Figure 21A:
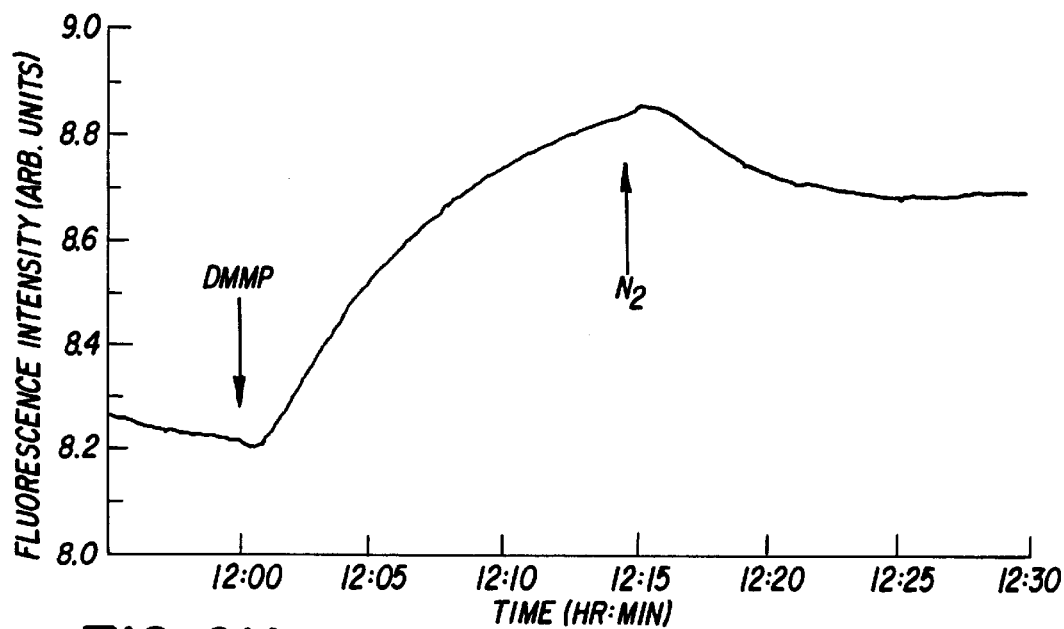
FIGS. 21A and 21B are graphs of the response of OX170/FP to DMMP vapor before and after coating the polymer (a trademark thereof is TEFLON with tetrafluoroethylene fluorocarbon AF, respectively.
Figure 21B:
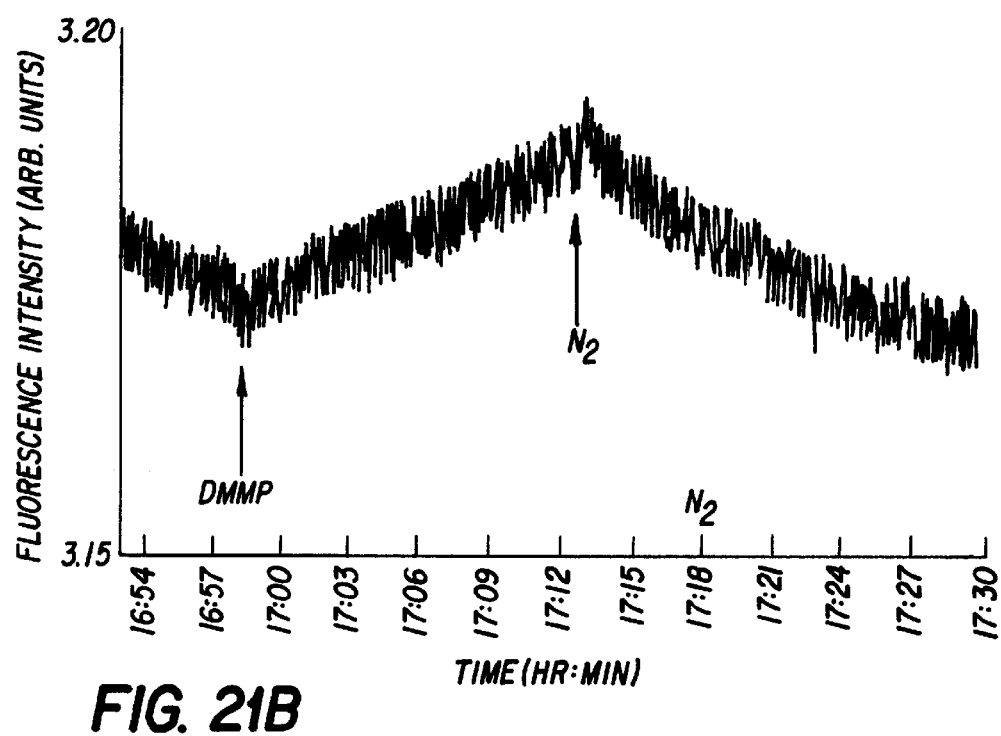
Figure 22:
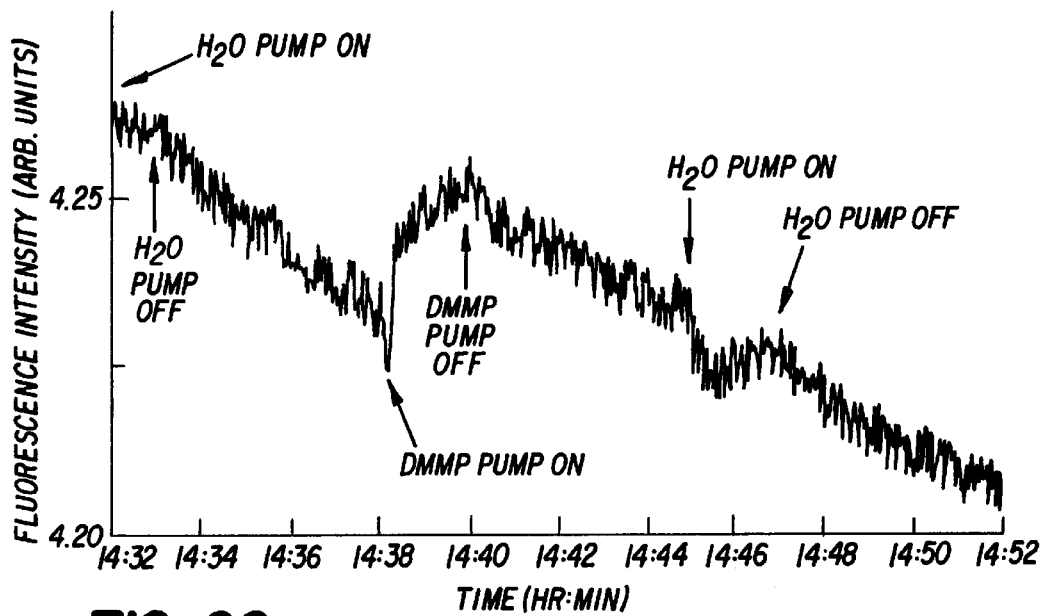
FIG. 22 is a graph of the response of TEFLON AF coated OX170/FP to 0.2 $\mu$l/ml DMMP in water.
Figure 23:
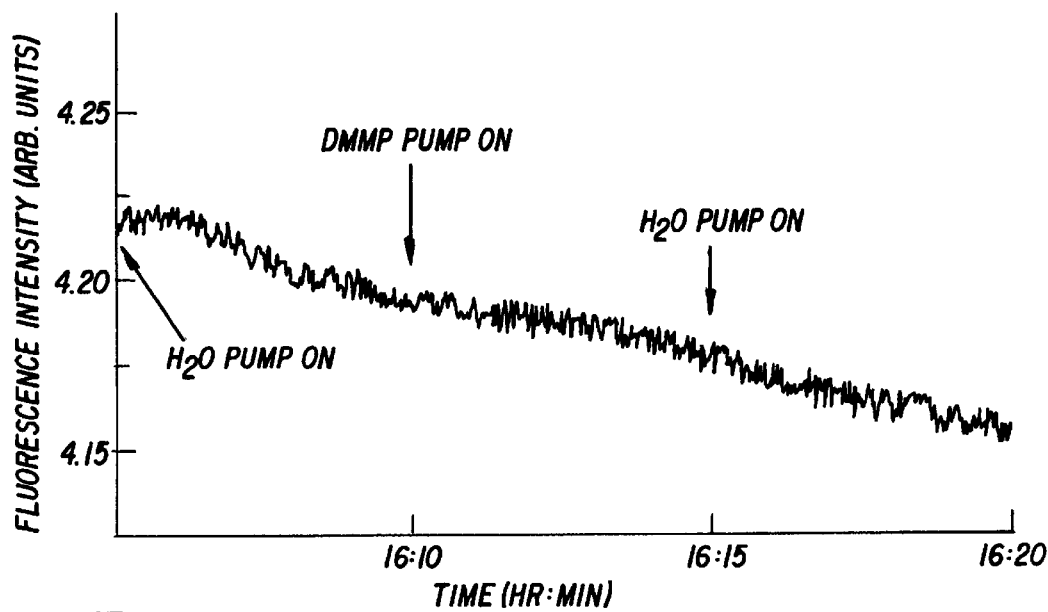
FIG. 23 is a graph of the response of TEFLON AF coated OX170/FP to 2 $\mu$l/ml DMMP in water.

FIGS. 21A and 21B show the response of a OX170/FP film (Type B film, TEFLON AF) to vapor phase DMMP before and after deposition of TEFLON coating. Note the decrease in sensitivity and increase in response time. This coated film was tested with DMMP in water with concentrations of 0.2 and 2 $\mu l$/ml of water (FIGS. 22 and 23).

Figure 24:
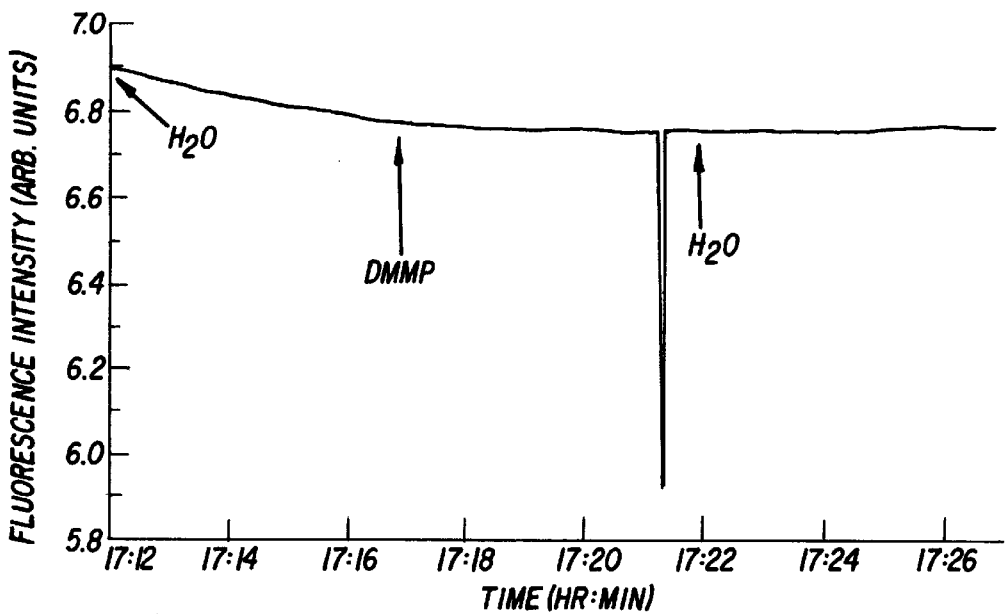
FIG. 24 is a graph of the response of TEFLON sheet coated OX170/FP to 2 μl/ml DMMP in water.

FIG. 24 shows the response of an OX170/FP film (Type C film, TEFLON sheet) having a TEFLON vapor barrier to DMMP under water. Although a response was observed, the fluorescence signal did not return to original level indicating that this probe may not be reversible or that the response time may be very long.

Table IX below summarizes the results of experiments that have been performed on Type A, B and C films, their projected sensitivity, advantages and disadvantages of each type of film.

The thickness of thin films is optimized for DMMP detection. Optimization of the film involves varying the thicknesses of the films to provide a reasonable fluorescence signal-to-noise ratio, a fast rise time and the highest sensitivity. Thin films of OX170/Fluoropolyol at a starting fluorophore concentration of $10^{-5}M$ and a polymer concentration of 0.48 wt % were used. More than 10 thin films of this combination have been made by spin coating and drop casting methods. The thicknesses of the films are varied by changing the spin rate or by changing the amount of dye/polymer solution used, respectively. Experiments indicate that spin coating produces very thin films (thickness on the order of nanometers), while drop casting produces thicker films on the order of hundreds of nanometers. To determine the exact thicknesses of these films would require the use of a multi-spectral ellipsometer.

Figure 25:
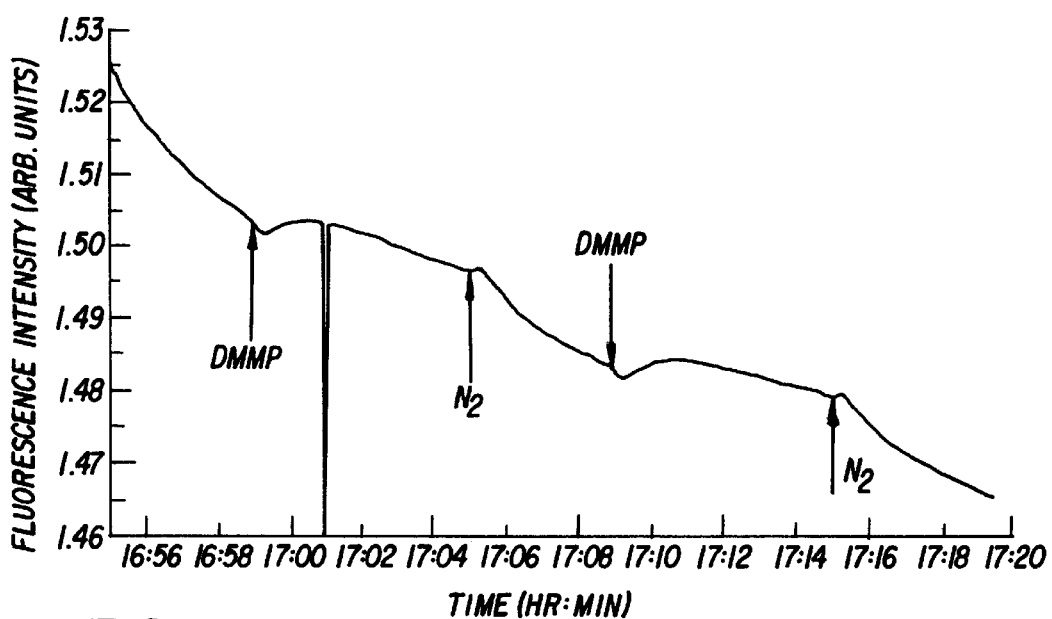
FIG. 25 is a graph of the response of OX170/FP film coated with a 58 μl solution tp 3.4 ppb DMMP vapor.
Figure 26:
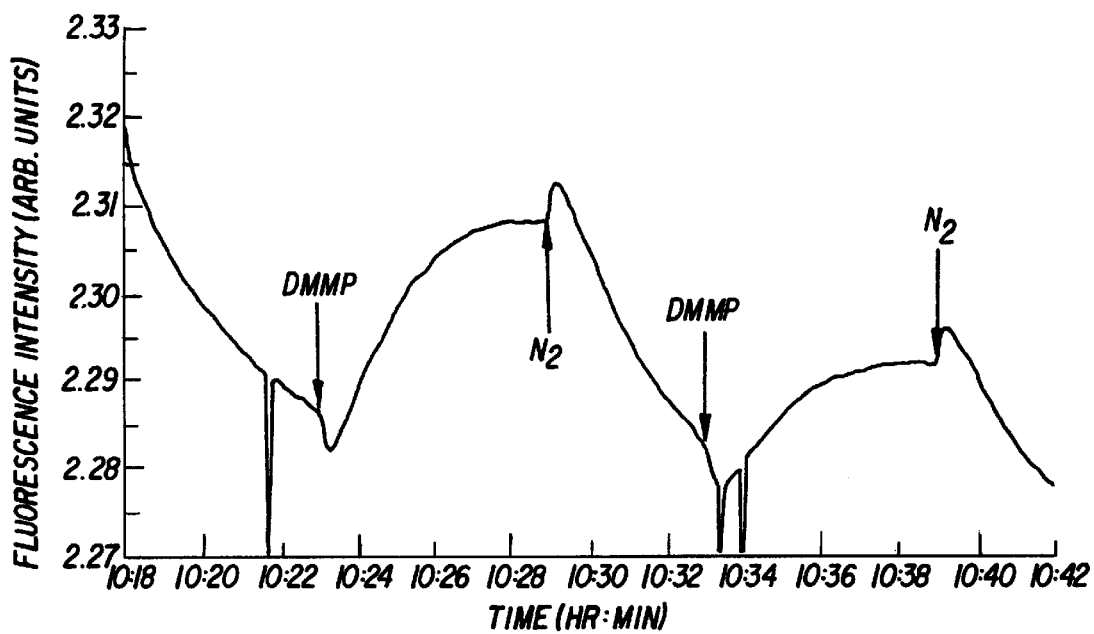
FIG. 26 is a graph of the response of OX170/FP film coated with a 100 μl solution to 4.2 ppb DMMP vapor.
Figure 27:
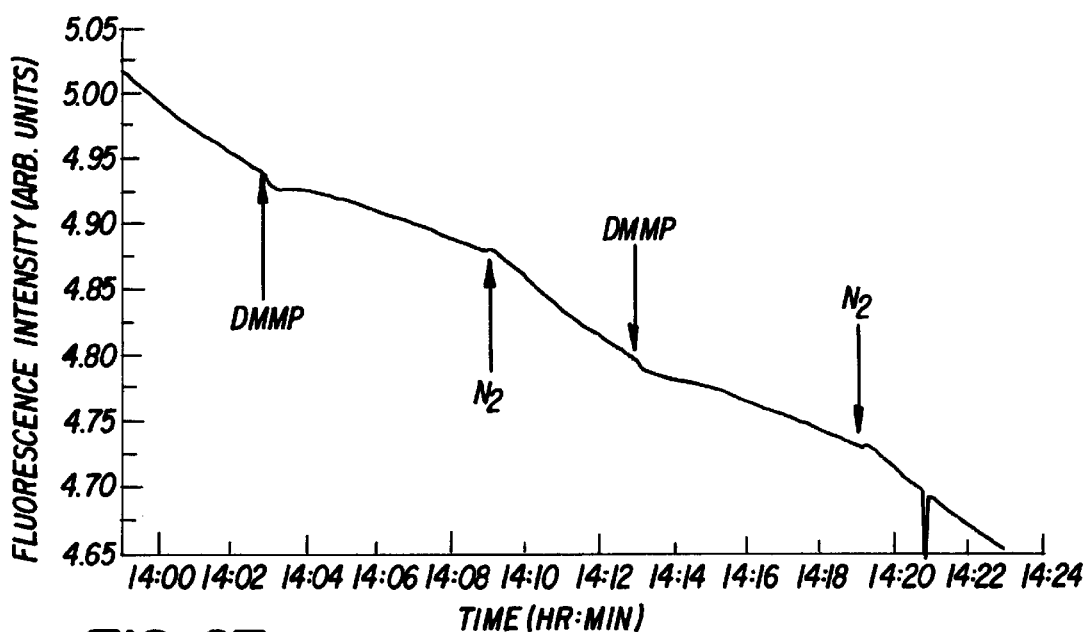
FIG. 27 is a graph of the response of OX170/FP film coated with a 300 μl solution to 3.4 ppb DMMP vapor.

FIGS. 25, 26 and 27 show the response of OX170/FP films having three different thicknesses to 3.4 ppb of DMMP vapor. The volume of the starting solutions used are 58, 100 and 300 $\mu l$, respectively. These figures show that the OX170/FP film prepared from 100 $\mu l$ solution had the highest sensitivity to DMMP vapor, and that the thinnest film prepared from 58 $\mu l$ solution had the fastest response time. The film that was prepared using the largest volume of solution had the slowest response time and the largest downward drift. These results show that there exists an optimum film thickness that leads to the highest sensitivity to agents. Table X lists the estimated detection limits for vapor phase DMMP.

The present invention detects chemical warfare agents at concentrations amenable to personnel protection, battlefield and facility monitoring, decontamination and decommissioning activities and treaty verification. An optical sensor system has been demonstrated to detect nerve agent GD (Soman) at concentrations less than 50 parts-per-billion with response time and cleardown times of less than 1 minute, and to differentiate that analyte from either mustard (HD) or VX. An improved miniature TIRF instrument shows sensitivity to dimethyl methylphosphonate (DMMP) at concentrations of 1.2 parts-per-billion, indicating sufficient signal-to-noise ratio to expect detection at 500 parts-per-trillion. Although the TIRF instrument required nearly one minute to come to full response to the simulant challenge, detection at 1.2 parts-per-billion against the baseline drift was within 10 seconds. This is an advance on the state-of-the-art in detection of chemical warfare agents in that there is no known low-cost instrument system providing response to this level of chemical agent in as short a time. Sorbent polymers having solvation parameters matched to analyte challenge vapors are used in providing a selective response to chemical warfare agents.

A miniature optical chemical sensor, based on the fluorescence of a fluorophore-polymer film, uses a diode laser for excitation and an amplified photodiode for detection. The instrument was fabricated for use with replaceable microscope slides having a fluorophore-polymer coating on the surface exposed to the vapor challenge. The microscope slides are manufactured with a bevel on the inlet face of the slide. The bevel is a suitable means of coupling light into the slide, and that instrument performance was comparable to that obtained using prism coupled slides.

The TIRF instrument compared well with a previous TIRF instrument comprised of a Hewlett-Packard Gain-Phase Detector. That indicates that instrument miniaturization may be achieved with little or no decrease of sensitivity to the levels tested thus far. Problems associated with instrument drift are likely the result of thermal effects within the fluorophore polymer film. Further improvements in instrument design are possible with optimization of slide bevel angle, angle of incidence of the laser beam and the refractive index of the slide and coatings on the slide.

Immobilization of fluorophores in polymeric matrices having known solvation parameters matched to the chemical warfare analytes of interest provide improved sensitivity over probes fabricated with the same fluorophores in polymers with little or no affinity to the agent of interest. That demonstrates the compatibility of surface acoustic wave sensor data with the selection of polymers suitable for optical detection of chemical warfare agents. Polymer materials such as fluoropolyol (FP), poly(epichlorohydrin) (PECH) respond differentially to Soman (GD) and sulfur Mustard (HD), and may be used in conjunction with fluorescent dyes to fabricate probes that are selective to chemical agents and interferents. Reversible probes may be produced using a range of fluorophores immobilized in polymers with an affinity for the threat of interest. Probes fabricated from FP respond reversibly to DMMP and GD. Near-infrared excited fluorophores are used to detect chemical and biological warfare materials.

Lock-in amplification may be used to decrease the lower limit of detection of the TIRF instrument for chemical agent simulants. Acquisition of fluorescence data in a field-based environment requires the design of instrumentation for stray light reduction and the use of lock-in or phase-based detection methods to separate the signal from the noise. The detection of fluorescence from fluorophore-polymer thin films using an amplified photodiode detector requires considerable amplification and separation of the scattering signal from the fluorescence signal. A temperature monitor (fluorescence-based or a thermocouple) may be included to reduce the effects of thermal drift on TIRF response.

Several polymer-fluorophore systems show selectivity, sensitivity and rapid response to chemical warfare agents and simulants when excited by semiconductor diode lasers. An angle of 20 degrees from the laser beam to the bevel surface is optimal. Vapor streams containing reference air and reference air with agent must be equalized with respect to all experimental variables, including vapor and probe temperature, relative humidity (water vapor concentration) and flow velocity, in order to achieve a repeatable test result. Over 120 slides containing fluorophore-polymer pairs have been developed. Less than 50 parts-per-billion of Soman (GD), less than 25 parts-per-billion of sulfur mustard (HD) and less than 200 parts-per-billion of VX are detectable using thin film probes of Oxazine 170 in fluoropolyol and Nile blue in poly(epichlorohydrin). The agents are distinguishable using those two probes. A fluorophore-polymer combination found to be extremely sensitive to dimethyl methylphosphonate (DMMP) vapor was used to shown sensitivity to DMMP at approximately 200 parts-per-million in a liquid-phase test using an overcoating of hydrophobic TEFLON AF that is suspected of being a decent barrier to the diffusive transfer of DMMP.

The present invention may be used in the areas of environmental monitoring of selected waste sites, ground-water quality control, process evaluation and hazard analysis for quality control in the food processing industry, biotechnological and materials processing industries. The reduced cost and portability of the sensor offers advantages in process inspection, point-of-care medical diagnosis and in environmental site monitoring.

The TIRF may be used as the detector in a flow immunoassay sensor for environmental analysis. Fully 35% of that market will be comprised of immunological tests performed on site by 2005. In the area of biomedical testing, there is a great need for point-of-care monitoring of physiological conditions and disease-producing micro-organisms. In the food industry, there is a need for product quality control and distributed process control.

Detection of gases such as ammonia in water is critically important for biotechnology and aquacultural industrial applications. Further applications of an inexpensive water test instrument capable of sensitivity to part-per-billion levels may be found in semiconductor processing, industrial boiler feed, feedwater for food processing operations, solvent recovery and wastewater monitoring applications. Environmental applications of the sensor may be found in gasoline leakage from underground tanks (OEM approach) assurance of compliance with wastewater effluent standards upstream of municipal wastewater treatment plants (particularly secondary treatment processes). Development of miniaturized TIRF structures for pH monitoring is expected to effect the worldwide market for on-line analyzers.

The direct application of the TIRF in vapor phase detection is to ensure compliance with Occupational Safety and Health Administration requirements as brought forth in 29 C.F.R. § 1910. The need is to provide an instrument which tracks the 8-hour time weighted average of the concentration of selected analytes. First, the TIRF can be a direct competitor to the Figaro probe which is sensitive to a large range of analytes but not selective for any. The Figaro probe is low-cost and exhibits lower limits of detection in the parts-per-million range. A selective detector is marketed by Microsensor Systems, Inc. that incorporates a surface acoustic wave device within a portable gas chromatograph for detection of benzene, toluene, Xylene and ethylene oxide at concentrations from 1 part-per-billion to 1,000 part-per million. The market for selective detectors for industrial vapors includes the need for sensors for carbon monoxide, nitric oxide, nitrogen dioxide hydrogen sulfide, sulfur dioxide and hydrogen cyanide. Probe materials would need to be developed for each of these applications. Sensors may be developed for automotive applications such as cabin air control. A sensor that detects roadside pollutants and advises the driver to use a filtered air supply would be useful for travel in some parts of the United States (Northern New Jersey) and in many parts of the world (Rwanda). Similar detectors may be used for automotive exhaust (used at automotive cabin temperatures) and fuel vent vapor release (fugitive emissions).

These sensors may also find application to optimize ventilation control in commercial and residential buildings. Key indoor pollutants include environmental tobacco smoke biological contaminants, semi-volatile organic compounds, such as formaldehyde, pesticides and polycyclic aromatic hydrocarbons (PAH's), cleansers, copy machine chemicals and synthetic building materials.

Detection of hydrogen from large industrial batteries, fuel cells and electric vehicles is expected to be a significant market. Detectors for ethylene oxide used in hospitals and for industrial processing operations are also needed. Detection of formaldehyde and wood preservative vapors may find considerable market in residential applications.

Large markets exist for optical sensors incorporated in paints, coatings, polymers, composites and other solid materials to provide information of structural safety, permeability to various threats, corrosion resistance and temperature, pressure and other environmental parameters. The use of embedded fluorophores in ion-exchange resins and filters is also expected to provide a moderate market application.

While the invention has been described with reference to specific embodiments, modifications and variations of the invention may be constructed without departing from the scope of the invention, which is defined in the following claims.

We claim:

1. A detection device comprising a shaped optical element, a fluorophore deposited within an evanescent field of the shaped optical element, a diode laser operatively disposed relative to the shaped optical element and creating an evanescent field for excitation of the fluorophore and generation of fluorescence, and a photodetector positioned adjacent a surface of the optical element having an amplified diode capable of detecting the fluorescence at the surface of said optical element.

2. The device of claim 1, further comprising a focusing lens between the laser and the shaped optical element.

3. The device of claim 1, wherein the shaped optical element is a polymer material.

4. The device of claim 3, wherein the shaped optical element is formed by injection molding.

5. The device of claim 4, wherein the shaped optical element has a scratch/dig specification of 60/40 or better.

6. The device of claim 1, wherein the diode laser has an output wavelength of about 635 to about 1060 nm.

7. The device of claim 1, further comprising a flow cell, wherein the shaped optical element forms one side of the flow cell, wherein the fluorophore deposited on the shaped optical element as a fluorophore-polymerfilm, and wherein the flow cell has an inlet for allowing a material to be detected to interact with the fluorophore-polymer film, and an outlet.

8. The device of claim 7, further comprising a vaporization chamber connected to the inlet for vaporizing a liquid material before flowing the material as a vapor to the flow cell.

9. The device of claim 8, further comprising a thin film heater in the vaporization chamber for rapidly heating the liquid material to the vapor.

10. The device of claim 9, wherein the vaporization chamber further comprises an inlet valve connected to the inlet of the flow cell and an outlet valve capable of controlling expansion of the vapor into the flow cell for interacting with the fluorophore-polymerfilm.

11. The device of claim 8, further comprising sensors capable of monitoring the temperature and pressure within the vaporization chamber.

12. The device of claim 8, wherein the vaporization chamber is up to about 10 mm long, and up to about 500 microns wide and deep.

13. The device of claim 7, wherein at least two photodetectors are mounted on the flow cell.

14. The device of claim 13, wherein a reference segment of the fluorophore-polymer film has a coating effective to prohibit interaction with material to be detected.

15. The device of claim 14, wherein one photodetector monitors the fluorescence from the reference segment of the fluorophore-polymer film.

16. The device of claim 13, wherein the at least two photodetectors are capable of monitoring non-coated segments of the fluorophore-polymer film.

17. The device of claim 1, wherein the diode laser is modulated.

18. The device of claim 17, wherein the modulation frequency is about 1 kHz.

19. The device of claim 17, wherein the modulation frequency is between and including 500 Hz and 5000 Hz.

20. The device of claim 1, wherein the photodetector comprises a photodiode capable of collecting the fluorescence signal and an integrated amplifier capable of amplifying the fluorescence signal.

21. The device of claim 1, further comprising a lock-in amplifier connected to the amplified photodiode capable of further amplifying the fluorescence signal.

22. The device of claim 1, wherein the fluorophore is in a fluorophore-polymer film, which is drop cast on a surface of the shaped optical element.

23. The device of claim 22, wherein the volume drop cast is about 75 to about 200 $\mu l$.

24. The device of claim 1, further comprising an optical filter connected to the photodiode effective to restrict light at the excitation wavelength.

25. The device of claim 24, wherein the optical filter is a holographic filter.

26. A detection device comprising a shaped optical element, a fluorophore deposited within an evanescent field of the shaped optical element, a diode laser operatively disposed relative to the shaped optical element and creating an evanescent field for excitation of the fluorophore and generation of fluorescence, and a photodetector having an amplified diode capable of detecting the fluorescence from the surface of said optical element, wherein the shaped optical element is a microscope slide.

27. A detection device comprising a shaped optical element, a fluorophore deposited within an evanescent field of the shaped optical element, a diode laser operatively disposed relative to the shaped optical element and creating an evanescent field for excitation of the fluorophore and generation of fluorescence, and a photodetector having an amplified diode capable of detecting the fluorescence from the surface of a optical element, wherein the shaped optical element is polystyrene with a refractive index of about 1.59.

28. A detection device comprising a shaped optical element, a fluorophore deposited within an evanescent field of the shaped optical element, a diode laser operatively disposed relative to the shaped optical element and creating an evanescent field for excitation of the fluorophore and generation of fluorescence, and a photodetector having an amplified diode capable of detecting the fluorescence from a surface of said optical element, wherein the shaped optical element has a beveled edge and the laser output enters the shaped optical element through the beveled edge.

29. The device of claim 28, wherein an angle of the beveled edge is such that an angle between a normal to the beveled edge and the laser output is between about 10 and about 20 degrees.

30. The device of claim 28, wherein the beveled edge is formed by selecting from a group consisting of lithographic processing and injection molding.

31. The device of claim 28, wherein a plan area of the shaped optical element decreases as the distance from the beveled edge increases.

32. A detection device comprising a shaped optical element, a fluorophore deposited within an evanescent field of the shaped optical element, a diode laser operatively disposed relative to the shaped optical element and creating an evanescent field for excitation of the fluorophore and generation of fluorescence, and a photodetector having an amplified diode capable of detecting the fluorescence from a surface of said optical element, and a splitter attached to said laser.

33. The device of claim 32, wherein the splitter is selected from a group consisting of a beam-splitter, a line generator and a holographic beam splitter.

34. An analyte detector apparatus comprising a radiant energy transparent guide, a fluorophore that fluoresces in the presence of radiant energy and the analyte in a fluid, wherein the fluorophore is deposited in conjunction with a thin polymer layer on a surface of the guide, a flow cell partially surrounding the surface, fluid conduits having a fluid intake and a fluid exhaust connected to the fluid conduits capable of moving the fluid through the chamber, a mover connected to the fluid conduits capable of moving the fluid through the chamber, a radiant energy source connected to the guide capable of irradiating the guide and the fluorophore, and a detector positioned adjacent a surface of the optical element associated with the flow cell or the guide capable of detecting fluorescing of the fluorophore at a surface of said guide or said flow cell and thus detecting presence of the analyte.

35. The detector apparatus of claim 34, further comprising a vaporization chamber having an inlet valve and an outlet valve, wherein the inlet valve is connected to the intake and the outlet valve is connected to the sample chamber, a heater connected to the vaporization chamber for vaporizing fluid within the vaporization chamber, and wherein the mover further comprises a sequencer for opening the valves and subsequently closing the valves, energizing the heater and opening the outlet valve for transferring vapors from the vaporization chamber to the sample chamber.

36. The detector apparatus of claim 34, wherein the guide is an optically transparent plate having a bevel at one end, wherein the radiant energy source is a laser optically aligned with the bevel for directing laser energy into the transparent plate for reflecting the energy within the plate and leaking some of the energy through the surface and wherein the detector comprises a photodiode and an amplifier connected to the photodiode.

37. A method of detecting analytes comprising providing a transparent plate, providing on a surface of the plate a fluorophore that changes fluorescent reaction to photoexcitation in the presence of a target analyte, partially forming a flow cell with a surface of the plate, flowing a fluid into the flow cell, illuminating one end of the plate with a laser diode, internally reflecting light from the laser diode within the plate, contacting the fluorophore with the target analyte, changing fluorescent reaction of the fluorophore with the target analyte, exciting the fluorophore with light from the plate, and detecting, through a detector positioned adjacent a surface of the flow cell or the plate, fluorescence at the surface of the flow cell or the plate.

38. The method of claim 37, further comprising providing multiple distinct fluorophores in parallel stripes along the surface of the plate, splitting illumination from the laser diode into parallel beams, directing the parallel beams into the plate, and internally reflecting the parallel beams in the plate.

39. The method of claim 37, wherein the detecting comprises detecting the fluorescence with an amplified photodiode and further amplifying output of the photodiode with an integral lock-in amplifier.

40. The method of claim 37, further comprising providing a bevel on the one end of the plate and wherein the illuminating comprises directing laser light through the bevel into the plate.

41. The method of claim 37, wherein the providing a fluorophore comprises depositing a fluorophore in conjunction with a thin polymer layer on the surface.

42. The method of claim 37, further comprising introducing a liquid into an evaporation chamber, closing valves to and from the evaporation chamber, heating the evaporation chamber, vaporizing liquid therein, opening a valve from the evaporation chamber, and flowing vapor to the flow cell.

43. A detection device comprising a shaped optical element having a beveled edge, a fluorophore deposited within an evanescent field of said shaped optical element, a diode laser capable of directing radiant energy onto the beveled edge of the shaped optical element and a photodetector having an amplified diode capable of detecting fluorescence of the fluorophore.

44. The device of claim 43, further comprising a focusing lens between the laser and the shaped optical element.

45. The device of claim 43, wherein the shaped optical element is a microscope slide.

46. The device of claim 42, wherein the shaped optical element is a polymer material.

47. The device of claim 46, wherein the shaped optical element is formed by injection molding.

48. The device of claim 47, wherein the shaped optical element has a scratch/dig specification of 60/40 or better.

49. The device of claim 43, wherein the shaped optical element is polystyrene with a refractive index of about 1.59.

50. The device of claim 43, wherein the diode laser has an output wavelength of about 635 to about 1060 nm.

51. The device of claim 43, wherein an angle of the beveled edge is such that an angle between a normal to the beveled edge and the laser output is between about 10 and about 20 degrees.

52. The device of claim 43, wherein the beveled edge is formed by selecting from a group consisting of lithographic processing and injection molding.

53. The device of claim 43, wherein a plan area of the shaped optical element decreases as the distance from the beveled edge increases.

54. The device of claim 43, further comprising of flow cell, wherein the shaped optical element forms one side of the flow cell, wherein the fluorophore is deposited on the shaped optical element as a fluorophore-polymer film, and wherein the flow cell has an inlet capable of allowing a material to be detected to interact with the fluorophore-polymer film, and an outlet.

55. The device of claim 54, further comprising a vaporization chamber connected to the inlet capable of vaporizing a liquid material before flowing the material as a vapor to the flow cell.

56. The device of claim 55, further comprising a thin film heater in the vaporization chamber capable of rapidly heating the liquid material to the vapor.

57. The device of claim 56, wherein the vaporization chamber further comprises an inlet valve connected to the inlet of the flow cell and an outlet valve capable of controlling expansion of the vapor into the flow cell for interacting with the fluorophore-polymer film.

58. The device of claim 55, further comprising sensors capable of monitoring the temperature and pressure within the vaporization chamber.

59. The device of claim 55, wherein the vaporization chamber is up to about 10 mm long, and up to about 500 microns wide and deep.

60. The device of claim 54, wherein at least two photodetectors are mounted on the flow cell.

61. The device of claim 60, wherein a reference segment of the fluorophore-polymer film has a coating effective to prohibit interaction with material to be detected.

62. The device of claim 61, wherein one of the at least two photodetectors is capable of monitoring the fluorescence from the reference segment of the fluorophore-polymer film.

63. The device of claim 60, wherein the at least two photodetectors are capable of monitoring non-coated segments of the fluorophore-polymer film.

64. The device of claim 43, wherein the diode laser has a modulation frequency.

65. The device of claim 64, wherein the modulation frequency is about 1 kHz.

66. The device of claim 64, wherein the modulation frequency is between and including about 500 Hz and about 5000 Hz.

67. The device of claim 43, further comprising a splitter attached to said laser.

68. The device of claim 67, wherein the splitter is selected from a group consisting of a beam-splitter, a line generator and a holographic beam splitter.

69. The device of claim 43, wherein the photodetector comprises a photodiode capable of collecting the fluorescence signal and an integrated amplifier capable of ambling the fluorescence signal.

70. The device of claim 43, further comprising a lock-in amplifier connected to the amplified photodiode capable of further amplifying the fluorescence signal.

71. The device of claim 43, wherein the fluorophore is in a fluorophore-polymer film, drop cast on a surface of the shaped optical element.

72. The device of claim 71, wherein the volume drop cast on a surface is about 75 to about 200 $\mu$l.

73. The device of claim 43, further comprising an optical filter connected to the photodiode effective to restrict light to the excitation wavelength.

74. The device of claim 73, wherein the optical filter is a holographic filter.

75. An analyte detector apparatus comprising a radiant energy transparent guide having beveled edge, a fluorophore capable of fluorescing in the presence of radiant energy and the analyte in a fluid, the fluorophore being deposited in conjunction with a thin polymer layer on a surface of the guide, a flow cell partially surrounding the surface, fluid conduits having a fluid intake and a fluid exhaust connected to the fluid conduits capable of moving the fluid through the chamber, a mover connected to the fluid conduits capable of moving the fluid through the chamber, a radiant energy source capable of emitting radiant energy onto the beveled edge of the guide and a detector associated with the flow cell of the guide capable of detecting fluorescing of the fluorophore emitted from a surface of said guide or said flow cell in response to presence of the analyte and the radiant energy.

76. The detector apparatus of claim 75, further comprising a vaporization chamber having an inlet valve and an outlet valve, wherein the inlet valve is connected to the intake and the outlet valve is connected to the sample chamber, a heater connect ed to the vaporization chamber capable of vaporizing fluid within the vaporization chamber, and wherein the mover further comprises a sequencer capable of opening the valves and subsequently closing the valves, energizing the heater and opening the outlet valve to transfer vapors from the vaporization chamber to the sample chamber.

77. The detector apparatus of claim 75, wherein the radiant energy source is a laser, wherein radiant energy is reflected within the plate.

78. The detector apparatus of claim 75, wherein the detector comprises a photodiode and an amplifier connected to said photodiode.

79. A method of detecting analytes comprising providing a transparent plate with a beveled edge comprising, providing on a surface of a plate a fluorophore that undergoes a fluorescent reaction to photoexcitation in the presence of a target analyte, partially forming a flow cell within the surface of the plate, flowing a liquid into the flow cell, illuminating the plate through the beveled edge with a laser diode, internally reflecting light from the laser diode within the plate, contacting the fluorophore with the target analyte, exciting the fluorophore, and detecting fluorescence emitted from the surface of one of the flow cell or the plate.

80. The method of claim 79, further comprising providing multiple distinct fluorophores in parallel stripes along the surface of the plate, splitting illumination from the laser diode into parallel beams, directing the parallel beams into the plate, and internally reflecting the parallel beams in the plate.

81. The method of claim 79, wherein the detecting comprises detecting the fluorescence with an amplified photodiode and amplifying output of the photodiode with an integral lock-in amplifier.

82. The method of claim 79, wherein the providing a fluorophore comprises depositing a fluorophore in conjunction with a thin polymer layer on the surface.

83. The method of claim 79, further comprising introducing a liquid into an evaporation chamber, closing valves to and from the evaporation chamber, vaporizing the liquid inside the evaporation chamber, opening a valve from the evaporation chamber, and flowing vapor to the flow cell.

84. A detection device comprising a shaped optical element having a beveled edge, a fluorophore deposited within the shaped optical element, a diode laser capable of directing radiant energy onto the beveled edge of the shaped optical element and a photodetector having an amplified diode capable of detecting the fluorescence emitted from the surface of said optical element.

85. The device of claim 84, further comprising a focusing lens between the laser and the shaped optical element.

86. The device of claim 84, wherein the shaped optical element is a microscope slide.

87. The device of claim 84, wherein the shaped optical element is a polymer material.

88. The device of claim 87, wherein the shaped optical element is formed by injection molding.

89. The device of claim 88, wherein the shaped optical element has a scratch/dig specification of 60/40 or better.

90. The device of claim 84, wherein the shaped optical element is polystyrene with a refractive index of about 1.59.

91. The device of claim 84, wherein the diode laser has an output wavelength of about 635 to about 1060 nm.

92. The device of claim 84, wherein an angle of the beveled edge is such that an angle between a normal to the beveled edge and the laser output is between about 10 and about 20 degrees.

93. The device of claim 84, wherein the beveled edge is formed by selecting from a group consisting of lithographic processing and injection molding.

94. The device of claim 84, wherein a plan area of the shaped optical element decreases as the distance from the beveled edge increases.

95. The device of claim 84, further comprising a flow cell, wherein the shaped optical element forms one side of the flow cell, wherein the fluorophore deposited on the shaped optical element as a fluorophore-polymer film, and wherein the flow cell has an inlet capable of allowing a material to be detected to interact with the fluorophore-polymer film, and an outlet.

96. The device of claim 95, further comprising a vaporization chamber connected to the inlet capable of vaporizing a liquid material before flowing the material as a vapor to the flow cell.

97. The device of claim 96, further comprising a thin film heater in the vaporization chamber capable of rapidly heating the liquid material to the vapor.

98. The device of claim 97, wherein the vaporization chamber further comprises an inlet valve connected to the inlet of the flow cell and an outlet valve capable of controlling expansion of the vapor into the flow cell to interact with the fluorophore-polymer.

99. The device of claim 96, further comprising sensors capable of monitoring the temperature and pressure within the vaporization chamber.

100. The device of claim 96, wherein the vaporization chamber is up to about 10 mm long, and up to about 500 microns wide and deep.

101. The device of claim 95, wherein at least two photodetectors are mounted on the flow cell.

102. The device of claim 101, wherein a reference segment of the fluorophore-polymer film has a coating effective to prohibit interaction with material to be detected.

103. The device of claim 102, wherein one of the two photodetectors is capable of monitoring the fluorescence from the reference segment of the fluorophore-polymer film.

104. The device of claim 101, wherein the at least two photodetectors monitor non-coated segments of the fluorophore-polymer film.

105. The device of claim 84, wherein the diode laser has a modulation frequency.

106. The device of claim 105, wherein the modulation frequency is about 1 kHz.

107. The device of claim 105, wherein the modulation frequency is between and including about 500 Hz and about 5000 Hz.

108. The device of claim 84, further comprising a splitter attached to said laser.

109. The device of claim 108, wherein the splitter is selected from a group consisting of a beam-splitter, a line generator and a holographic beam splitter.

110. The device of claim 84, wherein the photodetector comprises a photodiode capable of collecting the fluorescence signal, and an integrated amplifier capable of amplifying the fluorescence signal.

111. The device of claim 84, further comprising a lock-in amplifier connected to the amplified photodiode capable of further amplifying the fluorescence signal.

112. The device of claim 84, wherein the fluorophore is in a fluorophore-polymer film, drop cast on a surface of the shaped optical element.

113. The device of claim 112, wherein the volume drop cast is about 75 to about 200 µl.

114. The device of claim 84, further comprising an optical filter connected to the photodiode effective to restrict light to the excitation wavelength.

115. The device of claim 114, wherein the optical filter is a holographic filter.

116. An analyte detector apparatus comprising a radiant energy transparent guide having a beveled edge, a fluorophore that fluoresces in the presence of radiant energy and the analyte in a fluid, the fluorophore being deposited in conjunction with a thin polymer layer on a surface of the guide, a flow cell partially surrounding the surface, fluid conduits having a fluid intake and a fluid exhaust connected to the fluid conduits capable of moving the fluid through the chamber, a mover connected to the fluid conduits capable of moving the fluid through the chamber, a radiant energy source capable of emitting radiant energy onto the beveled edge of the guide, and a detector associated with the guide or the flow cell capable of detecting fluorescing of the fluorophore emitted from a surface of said guide or said flow cell.

117. The detector apparatus of claim 116, further comprising a vaporization chamber having an inlet valve and an outlet valve, wherein the inlet valve is connected to the intake and the outlet valve is connected to the sample chamber, a heater connected to the vaporization chamber capable of vaporizing fluid within the vaporization chamber, and wherein the mover further comprises a sequencer capable of opening the valves and subsequently closing the valves, energizing the heater and opening the outlet valve to transfer vapors from the vaporization chamber to the sample chamber.

118. The detector apparatus of claim 116, wherein the radiant energy source is a laser, wherein radiant energy is reflected with the plate.

119. The detector apparatus of claim 116, wherein the detector comprises a photodiode and an amplifier connected to said photodiode.

\* \* \* \* \*